US009931283B2

(12) United States Patent
Gabbay

(10) Patent No.: US 9,931,283 B2
(45) Date of Patent: *Apr. 3, 2018

(54) METHODS AND MATERIALS FOR SKIN CARE

(71) Applicant: Cupron Inc., Richmond, VA (US)

(72) Inventor: Jeffrey Gabbay, Jerusalem (IL)

(73) Assignee: Cupron Inc., Richmond, VA (US)

( * ) Notice: Subject to any disclaimer, the term of this patent is extended or adjusted under 35 U.S.C. 154(b) by 6 days.

This patent is subject to a terminal disclaimer.

(21) Appl. No.: 15/184,080

(22) Filed: Jun. 16, 2016

(65) Prior Publication Data

US 2016/0287492 A1 Oct. 6, 2016

Related U.S. Application Data

(63) Continuation of application No. 11/667,095, filed as application No. PCT/IL2005/001171 on Nov. 9, 2005, now Pat. No. 9,403,041.

(30) Foreign Application Priority Data

Nov. 9, 2004 (IL) .......................................... 165118
Nov. 9, 2005 (IL) .......................................... 171852

(51) Int. Cl.
*A61K 8/19* (2006.01)
*A61K 8/02* (2006.01)
*A61K 8/73* (2006.01)
*A61Q 19/08* (2006.01)

(52) U.S. Cl.
CPC .............. *A61K 8/19* (2013.01); *A61K 8/0204* (2013.01); *A61K 8/0212* (2013.01); *A61K 8/731* (2013.01); *A61Q 19/08* (2013.01)

(58) Field of Classification Search
None
See application file for complete search history.

(56) References Cited

U.S. PATENT DOCUMENTS

| 252,524 | A | 1/1882 | Sagendorf |
|---|---|---|---|
| 415,213 | A | 11/1899 | Pick |
| 1,210,375 | A | 12/1916 | Decker |
| 1,947,451 | A | 2/1934 | Barber et al. |
| 2,395,015 | A | 2/1946 | Paul et al. |
| 3,014,818 | A | 12/1961 | Campbell |
| 3,300,336 | A | 1/1967 | Domenick et al. |
| 3,308,488 | A | 3/1967 | Schoonman |
| 3,341,645 | A | 9/1967 | Soichiro Horiuchi et al. |
| 3,385,915 | A | 5/1968 | Hamling |
| 3,432,589 | A | 3/1969 | Drisch |
| 3,494,995 | A | 2/1970 | Rainer et al. |
| 3,632,721 | A | 1/1972 | Takashi Asaeda |
| 3,632,722 | A | 1/1972 | Takashi Asaeda |
| 3,632,723 | A | 1/1972 | Takashi Asaeda |
| 3,663,182 | A | 5/1972 | Hamling |
| 3,716,615 | A | 2/1973 | Bauer et al. |
| 3,720,743 | A | 3/1973 | Stevens et al. |
| 3,769,060 | A | 10/1973 | Ida et al. |
| 3,821,163 | A | 6/1974 | Spivak |
| 3,860,529 | A | 1/1975 | Hamling |
| 3,875,141 | A | 4/1975 | Drisch |
| 4,072,784 | A | 2/1978 | Cirino et al. |
| 4,103,450 | A | 8/1978 | Whitcomb |
| 4,115,422 | A | 9/1978 | Welch et al. |
| 4,174,418 | A | 11/1979 | Welch et al. |
| 4,201,825 | A | 5/1980 | Ebneth |
| 4,206,514 | A | 6/1980 | Yamauchi |
| 4,219,602 | A | 8/1980 | Conklin |
| 4,278,435 | A | 7/1981 | Ebneth |
| 4,291,086 | A | 9/1981 | Auten |
| 4,292,882 | A | 10/1981 | Clausen |
| 4,297,117 | A | 10/1981 | Holter et al. |
| 4,317,856 | A | 3/1982 | Huthelker et al. |
| 4,345,101 | A | 8/1982 | Asano et al. |
| 4,361,532 | A | 11/1982 | Benal et al. |
| 4,366,202 | A | 12/1982 | Borovsky |
| 4,385,632 | A | 5/1983 | Odelhog |
| 4,390,522 | A | 6/1983 | Jacquet et al. |
| 4,390,585 | A | 6/1983 | Holden |
| 4,428,773 | A | 1/1984 | Krotz |
| 4,525,410 | A | 6/1985 | Hagiwara |
| 4,666,940 | A | 5/1987 | Bischoff et al. |
| 4,675,014 | A | 6/1987 | Sustmann et al. |
| 4,688,567 | A | 8/1987 | Kikuchi et al. |
| 4,710,184 | A | 12/1987 | Ehret |

(Continued)

FOREIGN PATENT DOCUMENTS

| DE | 4403016 A1 | 8/1995 |
|---|---|---|
| EP | 116825 A1 | 8/1984 |
| EP | 116865 | 8/1984 |
| EP | 0253663 A | 1/1988 |
| EP | 253653 | 1/1989 |
| EP | 0427858 A | 5/1991 |
| EP | 1272037 B1 | 3/2004 |
| EP | 1978138 A2 | 10/2008 |
| EP | 1657980 | 5/2009 |
| FR | 2692482 A1 | 12/1993 |
| FR | 1499358 A | 9/1996 |
| FR | 2764518 | 6/1997 |
| FR | 2901140 A1 | 11/2007 |
| GB | 415213 | 8/1934 |
| GB | 1382820 | 12/1971 |

(Continued)

OTHER PUBLICATIONS

US 7,284,669, 10/2007, Gabbay (withdrawn)

(Continued)

*Primary Examiner* — Robert A Wax
*Assistant Examiner* — William Craigo
(74) *Attorney, Agent, or Firm* — Bernard G. Pike; Pike IP Law, PLLC

(57) ABSTRACT

The invention provides a cosmetic method for, preventing, minimizing and removing wrinkles and providing for smoother and more robust skin surfaces comprising applying a material incorporating water-insoluble copper compounds which release $Cu^+$ ions, $Cu^{++}$ ions or combinations thereof upon contact with a fluid to a body surface to be treated.

17 Claims, 9 Drawing Sheets

(56) References Cited

U.S. PATENT DOCUMENTS

| | | |
|---|---|---|
| 4,769,275 A | 9/1988 | Inagaki et al. |
| 4,853,019 A | 8/1989 | White et al. |
| 4,900,618 A | 2/1990 | O'Connor et al. |
| 4,900,765 A | 2/1990 | Murabayashi et al. |
| 4,931,078 A | 6/1990 | Yamamoto |
| 4,983,573 A | 1/1991 | Bolt et al. |
| 4,999,240 A | 3/1991 | Brotz |
| 5,009,946 A | 4/1991 | Hatomoto et al. |
| 5,017,420 A | 5/1991 | Marikar et al. |
| 5,024,875 A | 6/1991 | Hill et al. |
| 5,066,538 A | 11/1991 | Huykman |
| 5,089,205 A | 2/1992 | Huang et al. |
| 5,135,913 A | 8/1992 | Pickart |
| 5,143,769 A | 9/1992 | Moriya et al. |
| 5,175,040 A | 12/1992 | Harpell et al. |
| 5,180,585 A | 1/1993 | Jacobson |
| 5,200,256 A | 4/1993 | Dunbar |
| 5,217,626 A | 6/1993 | Yahya et al. |
| 5,227,365 A | 7/1993 | Van Den Sype |
| 5,254,134 A | 10/1993 | Zhao et al. |
| 5,269,973 A | 12/1993 | Takahashi et al. |
| 5,280,796 A | 1/1994 | Rosenberger |
| 5,316,837 A | 5/1994 | Cohen |
| 5,316,846 A | 5/1994 | Pinsky et al. |
| 5,370,934 A | 12/1994 | Burch et al. |
| 5,399,425 A | 3/1995 | Burch |
| 5,405,644 A | 4/1995 | Ohsumi et al. |
| 5,407,743 A | 4/1995 | Clough et al. |
| 5,411,795 A | 5/1995 | Silverman |
| 5,458,906 A | 10/1995 | Liang |
| 5,492,882 A | 2/1996 | Doughty et al. |
| 5,503,917 A | 4/1996 | Hughes |
| 5,518,812 A | 5/1996 | Mitchnick et al. |
| 5,547,610 A | 8/1996 | Mortenson |
| 5,549,972 A | 8/1996 | Hsu et al. |
| 5,573,021 A | 11/1996 | Grofcsik et al. |
| 5,631,013 A | 5/1997 | Bergmann et al. |
| 5,690,922 A | 11/1997 | Mouri et al. |
| 5,744,222 A | 4/1998 | Sugihara |
| 5,827,524 A | 10/1998 | Hagiwara et al. |
| 5,848,592 A | 12/1998 | Sibley |
| 5,849,235 A | 12/1998 | Sassa et al. |
| 5,856,248 A | 1/1999 | Weinberg |
| 5,869,412 A | 2/1999 | Yenni, Jr. et al. |
| 5,871,816 A | 2/1999 | Tal |
| 5,881,353 A | 3/1999 | Kamigata et al. |
| 5,904,854 A | 5/1999 | Shmidt et al. |
| 5,939,340 A | 8/1999 | Gabbay |
| 5,981,066 A | 11/1999 | Gabbay |
| 6,013,275 A | 1/2000 | Konagaya et al. |
| 6,036,839 A | 3/2000 | Kohut et al. |
| 6,067,444 A | 5/2000 | Cannon et al. |
| 6,124,221 A | 9/2000 | Gabbay |
| 6,369,289 B1 | 4/2002 | Orr |
| 6,383,273 B1 | 5/2002 | Kepner et al. |
| 6,394,281 B2 | 5/2002 | Ritland et al. |
| 6,447,677 B2 | 9/2002 | King |
| 6,479,584 B1 | 11/2002 | Nakagawa et al. |
| 6,482,424 B1 | 11/2002 | Gabbay |
| 6,627,676 B1 | 9/2003 | George et al. |
| 6,681,765 B2 | 1/2004 | Wen |
| 6,733,556 B1 | 5/2004 | Luigi |
| 6,770,331 B1 | 8/2004 | Mielke et al. |
| 6,861,002 B2 | 3/2005 | Hughes |
| 6,989,342 B2 | 1/2006 | Yang |
| 7,169,402 B2 | 1/2007 | Gabbay |
| 7,192,602 B2 | 3/2007 | Fechner et al. |
| 7,296,690 B2 | 11/2007 | Gabbay |
| 7,364,756 B2 | 4/2008 | Gabbay |
| 7,626,072 B2 | 12/2009 | Mocadio |
| 7,666,829 B2 | 2/2010 | Mitts et al. |
| 2003/0134780 A1 | 7/2003 | Patt |
| 2003/0152610 A1 | 8/2003 | Rolf et al. |
| 2003/0198945 A1 | 10/2003 | Gabbay |
| 2003/0199018 A1 | 10/2003 | Gabbay |
| 2004/0105894 A1 | 6/2004 | Gupta |
| 2004/0167483 A1 | 8/2004 | Gabbay |
| 2004/0167484 A1 | 8/2004 | Gabbay |
| 2004/0167485 A1 | 8/2004 | Gabbay |
| 2004/0180093 A1 | 9/2004 | Burton et al. |
| 2004/0197386 A1 | 10/2004 | Gabbay |
| 2004/0208902 A1 | 10/2004 | Gupta |
| 2004/0210984 A1 | 10/2004 | Cohen |
| 2004/0247653 A1 | 12/2004 | Gabbay |
| 2005/0048131 A1 | 3/2005 | Gabbay |
| 2005/0049370 A1 | 3/2005 | Gabbay |
| 2005/0150514 A1 | 7/2005 | Gabbay |
| 2007/0184017 A1 | 8/2007 | Faryniarz et al. |
| 2007/0184079 A1 | 8/2007 | Gabbay |
| 2008/0193496 A1 | 8/2008 | Gabbay |
| 2008/0241530 A1 | 10/2008 | Gabbay |
| 2008/0255285 A1 | 10/2008 | Gabbay |
| 2008/0311165 A1 | 12/2008 | Gabbay |
| 2009/0010969 A1 | 1/2009 | Gabbay |
| 2014/0065196 A1 | 3/2014 | Gabbay |

FOREIGN PATENT DOCUMENTS

| | | |
|---|---|---|
| JP | 63088007 | 4/1988 |
| JP | 01046465 | 2/1989 |
| JP | 01246204 | 10/1989 |
| JP | 02161954 | 6/1990 |
| JP | 02-264069 A | 10/1990 |
| JP | 03113011 | 5/1991 |
| JP | 03-185154 A | 8/1991 |
| JP | 4011017 A | 1/1992 |
| JP | 4058876 A | 2/1992 |
| JP | 3097909 A | 4/1992 |
| JP | 04-240205 A | 8/1992 |
| JP | 04-281010 A | 10/1992 |
| JP | 05005108 | 1/1993 |
| JP | 05-86577 A | 4/1993 |
| JP | 05-163614 A | 6/1993 |
| JP | 52-092000 A | 11/1993 |
| JP | 8113874 A | 5/1996 |
| JP | 2003-518201 A | 6/2003 |
| JP | 2003-275024 A | 9/2003 |
| JP | 2003-528975 A | 9/2003 |
| JP | 2003-531315 A | 10/2003 |
| WO | 9415463 | 7/1994 |
| WO | 9806508 A1 | 2/1998 |
| WO | 9806509 A1 | 2/1998 |
| WO | 0075415 A1 | 12/2000 |
| WO | 0128337 A2 | 4/2001 |
| WO | 0174166 | 10/2001 |
| WO | 01741166 A1 | 10/2001 |
| WO | 0181671 | 11/2001 |
| WO | 03018495 | 3/2003 |
| WO | 03035973 A1 | 5/2003 |
| WO | 03055941 A1 | 7/2003 |
| WO | 03086478 A1 | 10/2003 |
| WO | 03088983 | 10/2003 |
| WO | 05020689 A1 | 3/2005 |
| WO | 06048879 A1 | 5/2006 |
| WO | 2007/046083 A2 | 4/2007 |
| WO | 08117277 A2 | 10/2008 |
| WO | 2011-051948 A2 | 5/2011 |
| WO | 2012/046229 A2 | 4/2012 |

OTHER PUBLICATIONS

Encyclopedia of Polymer Science and Technology, John Wiley & Sons, Inc. 8:651-666 and 9:580-598 (1968).

Gabbay et al., "Copper Oxide Impregnated Textiles with Potent Biocidal Activities", Journal of Industrial Textiles, vol. 35, No. 4, 323-35, 2006

Hands-on Science (H-Sci) Project: Chemical Safety Database, "Chemical Safety Data: Copper (I) oxide", Comenius—European Cooperation on School Education, downloaded on Jul. 13, 2007 from http://ptcl.chem.ox.ac.uk/-hmclhsci/chemicals/copper_1_oxide.html.

(56) References Cited

OTHER PUBLICATIONS

Hawley's Condensed Chemical Dictionary, 14th Edition, John Wiley & Sons, Inc., Definitions of cuprous oxide and cupric oxide, 2002.
"Israeli Breakthrough Mines Copper to Keep Bacteria Away," Israel21C (revised Feb. 21, 2007) Retrieved Dec. 18, 2008 from URL: http://www.israel121c.org/bin/en.jsp?enScript_PrintVersion.jsp&enDispWho=Articles%SE11172.
Luvata Building Materials, downloaded Jul. 13, 2007 from http://.luvata.com/Products-Services/Markets-We-Serve/Architecture-and-Building/Building-Materials/.
Marino et al., "Electrochemical Properties of Silver-Nylon Fabrics," J. Electrochem. Soc., 132(1):68-72 (1985).
Material Safety Data Sheet #C5971: Cuprous Oxide Number, Effective Date: Feb. 26, 2007, downloaded from http://www.jtbaker.com/msds/englishhtmllc5971.htm.
International Search Report dated Sep. 19, 2001 corresponding to Appl. No. PCT/IL01/00299.
Database WPI, Section Ch, Week 198913, Derwent Publications Ltd., London, GB; AN 1989-097521 & JP 01 046565 A (Oyamada M( (1989) abstract.
Database WPI, Section Ch, Week 198945, Derwent Publications Ltd., London, GB; AN 1989-329454 & JP 01 246204 A (Kuraray Co Ltd) (1988) abstract.
Database WPI, Section Ch. Week 199125, Derwent Publications Ltd., London, GB; AN 1991-183257 & JP 33 113011 A (Kuraray Co Ltd) (1991) abstract.
Material Safety Data Sheet # C5971: Cuprous Oxide Number, Effective Date: Feb. 26, 2007, downloaded from http://Utbaker.com/msds/englishhtml/c5971.htm.
International Search Report dated Dec. 14, 2004 corresponding to Application No. PCT/IL2004/000636.
International Search Report dated Mar. 21, 2006 corresponding to Application No. PCT/IL2005/001160.
International Preliminary Report on Patentability (Chapter) with Written Opinion dated May 8, 2007 corresponding to Application No. PCT/IL2005/001160.
Borkow, "Copper's Role in Wound Healing," Cupron, Inc., located at http://www.pedorthicnewswire.com/pdf/Copper%20Role%20in%20Wound%20Healing.pdf, May 2004, 12 pages.
Borkow et al., "Improvement of Facial Skin Characteristics using Copper Oxide Containing Pillowcases: A Double-Blind, Placebo-Controlled, Parallel, Randomized Study," International Journal of Cosmetic Science 31(6): 437-443 (2009).
Borkow et al., "Reducing the risk of skin pathologies in diabetics by using copper impregnated socks," Medical Hypotheses, 2009, vol. 73, pp. 883-886.
Borkow et al., "Molecular mechanisms of enhanced wound healing by copper oxide-impregnated dressings," Wound Repair and Regeneration, 2010, vol. 18, pp. 266-275.
Borkow, "Protection of Soldiers' Feet by Copper Oxide Impregnated Socks," Advances in Military Technology, Dec. 2013, vol. 8, No. 2, pp. 101-108.
Gorter et al., "Examination of the Cutaneous Absorption of Copper After the Use of Copper-Containing Ointments," American Journal of Therapeutics, 2004, vol. 11, pp. 453-458.
Gugumus F., in "Aspects of the stabilization mechanisms of phenolic antioxidants in polyolefins," Macromolecular Materials and Engineering, vol. 137 Issue 1, pp. 189-225 Published Online: Mar 12, 2003.
International Preliminary Report on Patentability for PCT Application No. PCT/IL2011/000769 dated May 22, 2013.
International Search Report and Written Opinion for PCT Application No. PCT/IL2011/000769 dated Mar. 6, 2013.
Lower S. E., in "Calcium stearate in resins and resinous polymers: part 2", Pigment & Resin Technology, vol. 25 Iss: 2, Abstract only, 1996.
Merriam-Webster, "Definition of Copper Oxide," located at http://www.merriam-webster.com/dictionary/copper%20oxide, last visited on Aug. 7, 2014, 1 page.

Office Action of Japanese Patent Application No. 53971512007 dated May 31, 2011, English Translation only, 4 pages.
Office Action of Japanese Patent Application No. 53971512007 dated Dec. 6, 2011, English Translation only, 2 pages.
Office Action of Japanese Patent Application No. 53971512007 dated May 12, 2013, English Translation only, 6 pages.
Patravale et al., "Novel Cosmetic Delivery Systems: An Application Update," International Journal of Cosmetic Science 30(1): 19-33 (2008).
Rabe et al., "Photoaging: Mechanisms and Repair," Journal of the American Academy of Dermatology 55(1): 1-19 (2006). (abstract only).
Webster Online Dictionary, "Petrolatum," located at http://www.websters-online dictionary.org/definitions/petrolatum?cx=partner-pub-0939450753529744%3AvOqd01-tdlq &cof=FORID%3A9ie=UTF-8&q=petrolatum&sa=Search#906m, last visited on Aug. 2, 2015, 5 pages.
Wounds International, "Best Practice Guidelines: Wound Management in Diabetic Food Ulcers," located at www.woundsinternational.com, 2013.
Zatcoff et al., "Treatment of tinea pedis with socks containing copper oxide impregnated fibers," The Foot, 2008, vol. 18, pp. 136-141.
Borkow et al. "A Novel Anti-Influenza Copper Oxide Containing Respiratory Face Mask," PloS One, 2010, vol. 5, No. 6, pp. e11295, 8 pages total.
Borkow et al., "Copper Oxide Impregnated Wound Dressing: Biocidal and Safety Studies," Wounds, 100, vol. 22, No. 12, pp. 301-310, 2010 (Jun. 28, 2017).
Fogelgren et al., "Cellular Fibronectin Binds to Llysyl Oxidase with High Affinity and is Critical for Its Proteolytic Activation," Journal of Biological Chemistry, Jul. 1, 2005, vol. 280, No. 26, pp. 24690-24697.
Royce et al., "Reduced lysyl oxidase activity in skin fibroblasts from patients with Menke's syndrome," Biochem J, 1980, vol. 192, pp. 579-586.
Rucker et al., "Copper, lysyl oxidase, and extracellular matrix protein cross-linking," Am J Clin Nutr, 1998, vol. 67, pp. 996S-1002S.
Sen et al., "Cooper-induced vascular endothelial growth factor expression and wound healing," Am J Physiol Heart Circ Physiol, 2002, vol. 282, pp. H1281-H1827.
Uauay et al., "Essentiality of copper in humans," Am J Clin Nutr, 1998, vol. 67, pp. 952S-959S.
Delgado et al., "Polypropylene with Embedded Copper Metal or Copper Oxide Nanoparticles as a Novel Plastic Antimicrobial Agent," Letters in Applied Microbiology 53(1): 50-54 (2011).
Elguindi et al., "Metallic Copper Corrosion Rates, Moisture Content, and Growth Medium Influence Survival of Copper Ion-Resistant Bacteria," Applied Microbiology and Biotechnology, 89(6): 1963-1970 (2011).
Ren et al., "Preliminary Study of Anti-Infective Function of a Copper-Bearing Stainless Steel," Materials Science and Engineering: C, 32(1): 1204-1209 (2012).
Santo et al., "Antimicrobial Metallic Copper Surfaces Kill *Staphylococcus haemolyticus* via Membrane Damage," MicrobiologyOpen, 1(1): 46-52 (2012).
Santo et al. "Bacterial Killing by Dry Metallic Copper Surfaces," Applied and Environmental Microbiology, 77(3): 794-802 (2011).
Sunada et al. "Highly Efficient Antiviral and Antibacterial Activities of Solid-State Cuprous Compounds," Journal of Hazardous Materials, 235-236: 265-270 (2012).
Warnes and Keevil, "Mechanism of Copper Surface Toxicity in Vancomycin-Resistant Enterococci Following Wet or Dry Surface Contact," Applied and Environmental Microbiology, 77(17): 6049-6059 (2011).
Hydrophobic Polymers, Sigma-Aldrich, 2014.
Pickart, Reversing Skin Ageing with Copper Peptides, Body Language Dermatology, 2003. Obtained from http://web.archive.org/web/20030811100573l/http://www.skinbiology.com/bldermatology.html.
Office Action of Japanese Patent Application No. 53971512007 dated Oct. 23, 2012, English Translation only, 5 pages.

| Candidate ID | Day 1 | Week 1 | Week 2 | Week 4 |
|---|---|---|---|---|
| #1 | A x 10 | 2-A, 7-B, 1-C | 2-B, 7-C, 1-D | 1-B, 9-D |
| #2 | A x 10 | 1-A, 9-B | 7-B, 2-C, 1-D | 3-C, 7-D |
| #3 | A x 10 | 1-A, 8-B, 1-C | 8-C, 2-D | 10-D |
| #4 | A x 10 | 4-A, 6-B | 6-B, 4-C | 10-C |
| #5 | A x 10 | 2-A, 8-B | 10-B | 3-B, 3-C, 4-D |
| #6 | A x 10 | 9-B, 1-C | 4-B, 6-C | 3-C, 7-D |
| #7 | A x 10 | 2-A, 5-B, 3-C | 9-B, 1C | 8-C, 2-D |
| #8 | A x 10 | 4-B, 6-C | 9-C, 1-D | 2-C, 8-D |
| #9 | A x 10 | 6-B, 4-C | 7-C, 3-D | 10-D |
| #10 | A x 10 | 9-B, 1-C | 4-C, 6-D | 1-C, 9-D |
| #11 | A x 10 | 6-A, 4-B | 1-A, 6-B, 5-C | 10-C |
| #12 | A x 10 | 4-A, 6-B | 1-A, 9B | 2-B, 8-C |
| #13 | A x 10 | 10-B | 2B, 8-C | 10-D |
| #14 | A x 10 | 7-A, 3-B | 5-B, 5-C | 5-C, 5-D |
| #15 | A x 10 | 10-B | 1-B, 9-C | 2-C, 8-D |
| #16 | A x 10 | 9-B, 1-C | 8-C, 2-D | 2-C, 8-D |
| #17 | A x 10 | 8-B, 2-C | 7-C, 3-D | 10-D |

A = No Improvement
B = Slight Improvement
C = Improvement
D = Marked Improvement The letter in the box represents the condition as above and the number after that letter specifies the number of judges who saw a change.

FIGURE 11

METHODS AND MATERIALS FOR SKIN CARE

RELATED APPLICATIONS

This application is a continuation application filed under 35 U.S.C. 120 claiming priority to U.S. patent application Ser. No. 11/667,095 having a filing date of Jul. 9, 2008 which is national stage entry of International Patent Application No. PCT/IL2005/001171 with an International filing date of Nov. 9, 2005 and claims priority to Israel Patent Application No. 171,852 having a filing date of Nov. 9, 2005, and Israel Patent Application No. 165,118 having a filing date of Nov. 9, 2004.

TECHNICAL FIELD OF THE INVENTION

Polymeric materials for cosmetic applications including treatment of a face and/or neck of a subject identified as in need of reduction in wrinkles, fine lines, and/or crow's feet on the face or neck and methods of treating a face and/or neck of a subject identified as in need of reduction in wrinkles, fine lines, and/or crow's feet on the face or neck are described.

The present invention relates to a cosmetic method for minimizing, preventing and removing wrinkles and providing for smoother and more robust skin surfaces, and to the use of materials incorporating water-insoluble copper compounds for minimizing, preventing and removing wrinkles and providing for smoother and more robust skin surfaces and providing for smoother and more robust skin surfaces.

More particularly the present invention relates to a cosmetic method for minimizing, preventing and removing wrinkles and providing for smoother and more robust skin surfaces comprising applying a material incorporating water-insoluble copper compounds which release $Cu^+$ ions, $Cu^{++}$ ions or combinations thereof upon contact with a fluid to a body surface to be treated.

The invention also relates to the use of water-insoluble copper compounds which release $Cu^+$ ions, $Cu^{++}$ ions or combinations thereof upon contact with a fluid for the manufacture of a material such as a fabric or an extruded film, filament or sheath to be brought into contact with a body surface for preventing, minimizing and removing wrinkles and providing for smoother and more robust skin surfaces The sheath or extruded film can be of the new types of a monolithic layer with moisture removal properties or micro pores.

In addition the present invention relates to the use of a polymeric film having microscopic water insoluble particles of ionic copper oxides in powdered form, embedded directly therein with a portion of said particles being exposed and protruding from surfaces thereof, which particles release $Cu^+$ ions, $Cu^{++}$ ions or combinations thereof upon contact with a fluid for the manufacture of a material for preventing, minimizing and removing wrinkles and providing for smoother and more robust skin surfaces.

Similarly, the present invention relates to the use of fibers incorporating water-insoluble copper compounds which release $Cu^+$ ions, $Cu^{++}$ ions or combinations thereof upon contact with a fluid for the manufacture of a material for preventing, minimizing and removing wrinkles and providing for smoother and more robust skin surfaces.

In preferred embodiments of the present invention, as described hereinafter, said fibers are polymeric fibers having said compounds incorporated therein and protruding from the surfaces thereof.

In other preferred embodiments of the present invention, as described hereinafter, said fibers are coated with said copper compounds In further preferred embodiments of the present invention said material is formed from a polymeric component selected from the group consisting of a polyamide, a polyester, an acrylic and a polyalkylene, which would also include such materials as polypropylene, polyurethane, polyolefin, polyethylene, and other hydrophilic and hydrophobic polymers said material being in the form of a fiber, a yarn, or a sheet.

As will be described hereinafter with reference to the examples and the accompanying figures, it has now been surprisingly discovered that materials incorporating water-insoluble copper compounds which release $Cu^+$ ions, $Cu^{++}$ ions or combinations thereof upon contact with a fluid can be used for the manufacture of a fabric, a film, a filament or a sheath to be brought into contact with a body surface for the cosmetic use of preventing, minimizing and removing wrinkles and providing for smoother and more robust skin surfaces More specifically, it has now been surprisingly found that the materials of the present invention are effective in preventing, minimizing and removing wrinkles and providing for smoother and more robust skin surfaces.

There is available on the market a cream for topical application, which includes an organic copper peptide as a component thereof. As will be realized however, said cream is designed to penetrate the skin and the system in light of the linkage of the copper within an organic copper peptide, and said product therefore would not teach or suggest to a person skilled in the art that water-insoluble copper compounds which release $Cu^+$ ions, $Cu^{++}$ ions or combinations thereof upon contact with a fluid can be used for the manufacture of a fabric, a film, a filament or a sheath to be brought into contact with a body surface for the cosmetic use of preventing, minimizing and removing wrinkles and providing for smoother and more robust skin surfaces In both WO 98/06508 and WO 98/06509 there are taught various aspects of a textile with a full or partial metal or metal oxide plating directly and securely bonded to the fibers thereof, wherein metal and metal oxides, including copper, are bonded to said fibers.

More specifically, in WO 98/06509 there is provided a process comprising the steps of: (a) providing a metallized textile, the metallized textile comprising: (i) a textile including fibers selected from the group consisting of natural fibers, synthetic cellulosic fibers, regenerated fibers, acrylic fibers, polyolefin fibers, polyurethane fibers, vinyl fibers, and blends thereof, and (ii) a plating including materials selected from the group consisting of metals and metal oxides, the metallized textile characterized in that the plating is bonded directly to the fibers; and (b) incorporating the metallized textile in an article of manufacture.

In the context of said invention the term "textile" included fibers, whether natural (for example, cotton, silk, wool, and linen) or synthetic yarns spun from those fibers, and woven, knit, and non-woven fabrics made of those yarns. The scope of said invention included all natural fibers; and all synthetic fibers used in textile applications, including but not limited to synthetic cellulosic fibers (i.e., regenerated cellulose fibers such as rayon, and cellulose derivative fibers such as acetate fibers), regenerated protein fibers, acrylic fibers, polyolefin fibers, polyurethane fibers, and vinyl fibers, but excluding nylon and polyester fibers, and blends thereof.

Said invention comprised application to the products of an adaptation of technology used in the electrolyses plating of plastics, particularly printed circuit boards made of plastic, with metals. See, for example, Encyclopedia of Polymer Science and Engineering (Jacqueline I. Kroschwitz, editor), Wiley and Sons, 1987, vol. IX, pp 580-598. As applied to textiles, this process included two steps. The first step was the activation of the textile by precipitating catalytic noble metal nucleation sites on the textile. This was done by first soaking the textile in a solution of a low-oxidation-state reductant cation, and then soaking the textile in a solution of noble metal cations, preferably a solution of Pd++ cations, most preferably an acidic $PdCl_2$ solution. The low-oxidation-state cation reduces the noble metal cations to the noble metals themselves, while being oxidized to a higher oxidation state. Preferably, the reductant cation is one that is soluble in both the initial low oxidation state and the final high oxidation state, for example Sn++, which is oxidized to Sn++++, or Ti+++, which is oxidized to Ti++++.

The second step was the reduction, in close proximity to the activated textile, of a metal cation whose reduction was catalyzed by a noble metal. The reducing agents used to reduce the cations typically were molecular species, for example, formaldehyde in the case of Cu++. Because the reducing agents were oxidized, the metal cations are termed "oxidant cations" herein. The metallized textiles thus produced were characterized in that their metal plating was bonded directly to the textile fibers.

In WO 98/06508 there is described and claimed a composition of matter comprising:
(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and
(b) a plating including materials selected from the group consisting of metals and metal oxides;
the composition of matter characterized in that said plating is bonded directly to said fibers.

Said publication also claims a composition of matter comprising:
(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and
(b) a plurality of nucleation sites, each of said nucleation sites including at least one noble metal;
the composition of matter characterized by catalyzing the reduction of at least one metallic cationic species to a reduced metal, thereby plating said fibers with said reduced metal.

In addition, said publication teaches and claims processes for producing said products.

A preferred process for preparing a metallized textile according to said publication comprises the steps of:
a) selecting a textile, in a form selected from the group consisting of yarn and fabric, said textile including fibers selected from the group consisting of natural fibers, synthetic cellulosic fibers, regenerated protein fibers, acrylic fibers, polyolefin fibers, polyurethane fibers, vinyl fibers, and blends thereof;
b) soaking said textile in a solution containing at least one reductant cationic species having at least two positive oxidation states, said at least one cationic species being in a lower of said at least two positive oxidation states;
c) soaking said textile in a solution containing at least one noble metal cationic species, thereby producing an activated textile; and
d) reducing at least one oxidant cationic species in a medium in contact with said activated textile, thereby producing a metallized textile.

Said publications, however, were limited to coated fibers and textiles prepared according to said processes for the uses described therein, however said publications did not teach or suggest that such coated fibers and textiles could be effective for manufacture of a material for preventing, minimizing and removing wrinkles and providing for smoother and more robust skin surfaces.

Similarly said publications did not teach or suggest the possibility of incorporating cationic copper into a polymeric slurry of a hydrophobic polymer whereby there are produced films and fibers having microscopic particles of cationic copper encapsulated therein and protruding there from which have now also been surprisingly discovered as being effective for manufacture of material for preventing, minimizing and removing wrinkles and providing for smoother and more robust skin surfaces.

According to the description in U.S. Ser. No. 10/240,993, the teachings of which are incorporated herein by reference, it was discovered that by adding a small percentage of Cu++ in the form of water insoluble copper oxide particles to the slurry of a polymer to be formed, the resulting polymer possessed antimicrobial properties.

Furthermore it was surprisingly discovered and described therein that by adding copper oxide in particle form into a polymeric slurry of such polymers as polyethylene, polypropylene, polyesters and similar hydrophobic or hydrophilic polymeric materials it is possible to extrude fibers, yarns or sheets which possess both antimicrobial and antiviral properties which have a multiplicity of uses. Among the uses contemplated for the novel antimicrobial and antiviral polymeric materials described in said specification was their use in a backing for a carpet, which could even be used in a hospital setting since it would not develop mold, smell, and would inactivate any viruses settling thereon; the use as a component of a molded non-woven product such as an air filter in a hospital or airplane or a mask which could be made air permeable or liquid permeable and be used to filter fluids flowing there through and to inactivate bacteria and viruses found in said fluids; formation into a continuous, flat, textured or stretched form which could be used in articles of clothing such as stockings, socks, shirts or any article of clothing that would incorporate a hydrophobic polymeric fiber or yarn; formation of a short staple fiber which could be then used as is or blended with other fibers such as cotton, which blended yarns could then be used for the manufacture of a variety of both knit and woven products such as socks, sheets, etc.; and use of such polymeric materials, manufactured in the form of a bi-component yarn in which the core is one compound and the sheath around the core is a polymer containing the water insoluble copper oxide particles creating a yarn with a multitude of end uses in either a continuous, flat, textured, stretched form or as a short staple. An example of said latter use would be the use of a polyethylene core with a polymeric sheath incorporating said water insoluble copper oxide particles to form a yarn with an increased resistance to being cut or ripped while also being both antimicrobial and antiviral and having a multiplicity of uses including in the food preparation industry.

Said material was described as being made from almost any synthetic polymer, which will allow the introduction of an cationic, copper oxide particles into its liquid slurry state. Examples of some materials are polyamides (nylon), polyester, acrylic, and polyalkylenes such as polyethylene and polypropylene, When the copper oxide dust is ground down to fine powder, e.g., a size of between 1 and 10 microns and introduced into the slurry in small quantities, e.g., in an amount of between 0.25 and 10% of the polymer weight, in a master batch as is the accepted practice for manufacturing extruded fibers and films it was found that the subsequent product produced from this slurry exhibited both antimicrobial and antiviral properties.

Unlike the fibers described, e.g. in WO 98/06508 and WO 98/06509, in which the fibers are coated on the outside, in said product the polymer has microscopic water insoluble particles of cationic copper oxide encapsulated therein with a portion of said particles being exposed and protruding from surfaces thereof. These exposed particles which protrude from the surface of the polymeric material have been shown to be active, as demonstrated by the tests set forth in said specification, and the teachings thereof as they are relevant to the present invention are incorporated herein by reference.

Said US specification, however, also did not teach or suggest that the polymeric materials described therein are effective for manufacture of a material for preventing, minimizing and removing wrinkles and providing for smoother and more robust skin surfaces as described and exemplified herein.

In general, the products of said specification and also products which can be used in the present invention are produced as follows:

1. A slurry is prepared from any polymer, the chief raw material preferably being selected from a polyamide, a polyalkylene, a polyurethane and a polyester. Combinations of more than one of said materials can also be used provided they are compatible or adjusted for compatibility. The polymeric raw materials are usually in bead form and can be mono-component, bi-component or multi-component in nature. The beads are heated to melting at a temperature which preferably will range from about 120 to 180° C.
2. At the hot mixing stage, before extrusion, a water insoluble powder of cationic copper oxide is added to the slurry and allowed to spread through the heated slurry. The particulate size will be preferably between 1 and 10 microns, however can be larger when the film or fiber thickness can accommodate larger particles.
3. The liquid slurry is then pushed with pressure through holes in a series of metal plates formed into a circle or other desired shape called a spinneret. As the slurry is pushed through the fine holes that are close together, they form single fibers or if allowed to contact one another, they form a film or sheath. The hot liquid fiber or film is pushed upward with cold air forming a continuous series of fibers or a circular sheet. The thickness of the fibers or sheet is controlled by the size of the holes and speed at which the slurry is pushed through the holes and upward by the cooling air flow.

In WO 94/15463 there are described antimicrobial compositions comprising an inorganic particle with a first coating providing antimicrobial properties and a second coating providing a protective function wherein said first coating can be silver or copper or compounds of silver, copper and zinc and preferred are compounds containing silver and copper (II) oxide. Said patent, however, is based on the complicated and expensive process involving the coating of the metallic compositions with a secondary protective coating selected from silica, silicates, borosilicates, aluminosilicates, alumina, aluminum phosphate, or mixtures thereof and in fact all the claims are directed to compositions having successive coatings including silica, hydrous alumina and dioctyl azelate.

In contradistinction, the present invention is inter alia directed to the use of a polymeric material, having microscopic water insoluble particles of cationic copper oxide in powder form, which release $Cu^{++}$ encapsulated therein with a portion of said particles being exposed and protruding from surfaces thereof, which is neither taught nor suggested by said publication and which has the advantage that the exposed $Cu^{++}$ releasing water insoluble particles which protrude from the polymeric material have been proven to be effective in preventing, minimizing and removing wrinkles and providing for smoother and more robust skin surfaces.

In EP 427858 there is described an antibacterial composition characterized in that inorganic fine particles are coated with an antibacterial metal and/or antibacterial metal compound and said patent does not teach or suggest a polymer that incorporates microscopic water insoluble particles of cationic copper oxide in powder form, which release $Cu^{++}$ encapsulated therein with a portion of said particles being exposed and protruding from surfaces thereof.

In DE 4403016 there is described a bactericidal and fungicidal composition utilizing copper as opposed to ionic $Cu^{++}$ and said patent also does not teach or suggest a polymer that incorporates microscopic water insoluble particles of cationic copper oxide in powder form, which release $Cu^{++}$ encapsulated therein with a portion of said particles being exposed and protruding from surfaces thereof.

In JP-01 046465 there is described a condom releasing sterilizing ions utilizing metals selected from copper, silver, mercury and their alloys which metals have a sterilizing and sperm killing effect, wherein the metal is preferably finely powdered copper. While copper salts such as copper chloride, copper sulfate and copper nitrate are also mentioned, as is known, these are water soluble salts which will dissolve and break down the polymer in which they are introduced. Similarly, while cuprous oxide is specifically mentioned, this is a $Cu^+$ ionic form, and therefore said patent does not teach or suggest the use of exposed $Cu^{++}$ releasing water insoluble particles which protrude from the polymeric material and which have been proven to be effective in preventing, minimizing and removing wrinkles and providing for smoother and more robust skin surfaces.

In JP-01 246204 there is described an antimicrobial molded article in which a mixture of a powdery copper compound and organic polysiloxane are dispersed into a thermoplastic molded article for the preparation of cloth, socks, etc. Said patent specifically states and teaches that metal ions cannot be introduced by themselves into a polymer molecule and requires the inclusion of organopolysiloxane which is also intended to provide a connecting path for the release of copper ions to the fiber surface. Thus, as will be realized said copper compound will be encapsulated and said patent does not teach or suggest the use of exposed $Cu^{++}$ releasing water insoluble copper oxide particles that protrude from the polymeric material.

In JP-03 113011 there is described a fiber having good antifungal and hygienic action preferably for producing underwear wherein said synthetic fiber contains copper or a copper compound in combination with germanium or a compound thereof, however, said patent teaches and requires the presence of a major portion of germanium and the copper compounds disclose therein are preferably metallic copper, cuprous iodide which is a monovalent $Cu^+$ compound and water soluble copper salts. Thus, said patent does not teach or suggest the use of exposed $Cu^{++}$ releasing water insoluble copper oxide particles which protrude from the polymeric material.

In EP 116865 there is described and claimed a polymer article containing zeolite particles at least part of which retain at least one metal ion having a bacterial property and thus said patent does not teach or suggest the use of exposed $Cu^{++}$ releasing water insoluble copper oxide particles, by themselves and in the absence of a zeolite, which particles protrude from the polymeric material and which have been proven to be effective in preventing, minimizing and removing wrinkles and providing for smoother and more robust skin surfaces In EP 253653 there is described and claimed a polymer containing amorphous aluminosilicate particles comprising an organic polymer and amorphous aluminosilicate solid particles or amorphous aluminosilicate solid particles treated with a coating agent, at least some of said amorphous aluminosilicate solid particles holding metal ions having a bactericidal actions. Thus, said patent does not teach or suggest the use of exposed $Cu^{++}$ releasing water insoluble copper oxide particles, by themselves and in the absence of amorphous aluminosilicate particles, which exposed $Cu^{++}$ releasing water insoluble copper oxide particles, protrude from the polymeric material and which have been proven to be effective in preventing, minimizing and removing wrinkles and providing for smoother and more robust skin surfaces.

Thus none of said publications teach or suggest the use of water-insoluble copper compounds which release $Cu^+$ ions, $Cu^{++}$ ions or combinations thereof upon contact with a fluid for the manufacture of a fabric or an extruded film, filament or sheath to be brought in contact with a body surface for preventing, minimizing and removing wrinkles and providing for smoother and more robust skin surfaces.

Thus, one preferred aspect of the present invention relates to the use of fibers incorporating water-insoluble copper compounds which release $Cu^+$ ions, $Cu^{++}$ ions or combinations thereof upon contact with a fluid for manufacture of a material for preventing, minimizing and removing wrinkles and providing for smoother and more robust skin surfaces.

In preferred embodiments of said aspect of the invention, said material is formed of a fabric material or a substrate incorporating fibers treated with a cationic species of copper and incorporating water-insoluble copper compounds which release $Cu^+$ ions, $Cu^{++}$ ions or combinations thereof upon contact with a fluid.

It is to be noted that said fibers or substrate can be made of a hydrophilic or a hydrophobic polymeric material.

In preferred embodiments of said first aspect of the present invention, said fibers are polymeric fibers having said compounds incorporated therein and protruding from the surfaces thereof.

In other preferred embodiments of said aspect of the present invention said fibers are coated with said copper compounds.

A second preferred aspect of the present invention relates to the use of a polymeric film having microscopic water insoluble particles of ionic copper oxides in powdered form, embedded directly therein with a portion of said particles being exposed and protruding from surfaces thereof, which particles release $Cu^+$ ions, $Cu^{++}$ ions or combinations thereof upon contact with a fluid for the manufacture of a material for preventing, minimizing and removing wrinkles and providing for smoother and more robust skin surfaces.

A third preferred aspect of the present invention relates to the use of fibers incorporating water-insoluble copper compounds which release $Cu^+$ ions, $Cu^{++}$ ions or combinations thereof upon contact with a fluid for the manufacture articles of clothing to be worn for preventing, minimizing and removing wrinkles and providing for smoother and more robust skin surfaces.

Also in this third aspect of the present invention said fibers are preferably polymeric fibers having said compounds incorporated therein and protruding from the surfaces thereof or said fibers are coated with said copper compounds A fourth preferred aspect of the present invention relates to the use of a polymeric film having microscopic water insoluble particles of ionic copper oxides in powdered form, embedded directly therein with a portion of said particles being exposed and protruding from surfaces thereof, which particles release $Cu^+$ ions, $Cu^{++}$ ions or combinations thereof upon contact with a fluid for the manufacture of a tubular sheath for removable positioning on the neck of a user to be worn for preventing, minimizing and removing wrinkles and providing for smoother and more robust skin surfaces.

A fifth preferred aspect of the present invention relates to the use of fibers incorporating water-insoluble copper compounds which release $Cu^+$ ions, $Cu^{++}$ ions or combinations thereof upon contact with a fluid for the manufacture of a tubular sheath for removable positioning on the neck of a user to be worn for preventing, minimizing and removing wrinkles and providing for smoother and more robust skin surfaces.

Also in this fifth aspect of the present invention said fibers are preferably polymeric fibers having said compounds incorporated therein and protruding from the surfaces thereof or said fibers are coated with said copper compounds.

A sixth preferred aspect of the present invention relates to the use of fibers incorporating water-insoluble copper compounds which release $Cu^+$ ions, $Cu^{++}$ ions or combinations thereof upon contact with a fluid for the manufacture of a fabric for preventing, minimizing and removing wrinkles and providing for smoother and more robust skin surfaces.

Preferably said fabric can be used in a pillow case, a cover, a sheet or any textile article with which body surfaces prone to wrinkling can come in contact.

A seventh preferred aspect of the present invention relates to the use of fibers incorporating water-insoluble copper compounds which release $Cu^+$ ions, $Cu^{++}$ ions or combinations thereof upon contact with a fluid for the manufacture of socks for preventing, minimizing and removing wrinkles and providing for smoother and more robust skin surfaces.

An eighth preferred aspect of the present invention relates to the use of fibers incorporating water-insoluble copper compounds which release $Cu^+$ ions, $Cu^{++}$ ions or combinations thereof upon contact with a fluid for the manufacture of a terry cloth material for preventing, minimizing and removing wrinkles and providing for smoother and more robust skin surfaces.

Similarly in preferred embodiments of the present invention, said fabric can be in the form of a scarf to be worn around the neck and to tubular sheath for removable positioning on the neck of a user to be worn for preventing, minimizing and removing wrinkles and providing for smoother and more robust skin surfaces.

In further preferred embodiments of the present invention, said fabric can be in the form of an at least partial face mask.

Since there are people who are sensitive with regard to the wrinkled appearance of their hands, said fabric can also be in the form of gloves to be cosmetically worn for preventing, minimizing and removing wrinkles and providing for smoother and more robust skin surfaces on hand surfaces.

Also in these aspects of the present invention said fibers are preferably polymeric fibers having said compounds incorporated therein and protruding from the surfaces thereof or said fibers are coated with said copper compounds.

In another aspect of the present invention there is now provided a cosmetic method for preventing, minimizing and removing wrinkles and providing for smoother and more robust skin surfaces on skin surfaces comprising applying thereto a polymeric material formed from a polymeric component selected from the group consisting of a polyamide, a polyester, an acrylic and a polyalkylene, said material being in the form of a fiber, a yarn, a sheath, a filament, or a sheet, and having microscopic water insoluble particles of ionic copper oxides in powdered form, embedded directly therein with a portion of said particles being exposed and protruding from surfaces thereof, which particles release $Cu^+$ ions, $Cu^{++}$ ions or combinations thereof upon contact with a fluid.

In a first group of preferred embodiments of the present invention said material is a fabric having fibers incorporating water-insoluble copper compounds which release $Cu^+$ ions, $Cu^{++}$ ions or combinations thereof upon contact with a fluid.

In a second group of preferred embodiments said material is a polymeric film having microscopic water insoluble particles of ionic copper oxides in powdered form, embedded directly therein with a portion of said particles being exposed and protruding from surfaces thereof, which particles release $Cu^+$ ions, $Cu^{++}$ ions or combinations thereof upon contact with a fluid.

In a third group of preferred embodiments of the present invention said material is a polymeric fiber having microscopic water insoluble particles of ionic copper oxides in powdered form, embedded directly therein with a portion of said particles being exposed and protruding from surfaces thereof, which particles release $Cu^+$ ions, $Cu^{++}$ ions or combinations thereof upon contact with a fluid.

In a fourth group of preferred embodiments of the present invention said material is a polymeric filament having microscopic water insoluble particles of ionic copper oxides in powdered form, embedded directly therein with a portion of said particles being exposed and protruding from surfaces thereof, which particles release $Cu^+$ ions, $Cu^{++}$ ions or combinations thereof upon contact with a fluid.

In a fifth group of preferred embodiments of the present invention said material is a polymeric sheath having microscopic water insoluble particles of ionic copper oxides in powdered form, embedded directly therein with a portion of said particles being exposed and protruding from surfaces thereof, which particles release $Cu^+$ ions, $Cu^{++}$ ions or combinations thereof upon contact with a fluid.

In a sixth group of preferred embodiments of the present invention, said material is a polymeric film having microscopic water insoluble particles of ionic copper oxides in powdered form, embedded directly therein with a portion of said particles being exposed and protruding from surfaces thereof, which particles release Cu+ ions, Cu++ ions or combinations thereof upon contact with a fluid wherein said film has the ability to disperse liquid through osmosis.

In a seventh group of preferred embodiments of the present invention, said material is a polymeric film having microscopic water insoluble particles of ionic copper oxides in powdered form, embedded directly therein with a portion of said particles being exposed and protruding from surfaces thereof, which particles release Cu+ ions, Cu++ ions or a combination thereof upon contact with a fluid wherein said film has micro pores perforated throughout to allow for the escape of excess liquids.

As stated above, based on the surprising discovery of the present invention that a material incorporating water-insoluble copper compounds which release $Cu^+$ ions, $Cu^{++}$ ions or combinations thereof, upon contact with a fluid, can be used in a cosmetic method for preventing, minimizing and removing wrinkles and providing for smoother and more robust skin surfaces, many articles of manufacture can be prepared for cosmetic use for achieving this highly desirable result.

The polymeric materials for use in the present invention can be produced by preparing a slurry of a polymer selected from the group consisting of a polyamide, a polyester, an acrylic and a polyalkylene, and mixtures thereof, introducing a powder consisting essentially of water insoluble cationic copper oxides and dispersing the same in said slurry and then extruding said slurry to form a polymeric material wherein water insoluble copper oxide particles that release $Cu^{++}$ are encapsulated therein with a portion of said particles being exposed and protruding from surfaces thereof, which polymeric material is then formed into a fiber, a yarn or a sheet to be manufactured into a fabric suitable to be brought in contact with a body surface for preventing, minimizing and removing wrinkles and providing for smoother and more robust skin surfaces.

In U.S. Pat. No. 6,124,221 there is described and claimed an article of clothing having antibacterial, antifungal, and antiyeast properties, comprising at least a panel of a metalized textile, the textile including fibers selected from the group consisting of natural fibers, synthetic cellulosic fibers, regenerated protein fibers, acrylic fibers, polyolefin fibers, polyurethane fibers, vinyl fibers, and blends thereof, and having a plating including an antibacterial, antifungal and antiyeast effective amount of at least one oxidant cationic species of copper.

In said specification there was described that said article of clothing was effective against *Tinea Pedis*, against *Candida Albicans*, against Thrush and against bacteria causing foot odor, selected from the group of *brevubacterium, acinetobacter, micrococcus* and combinations thereof, however said patent did not teach or suggest that such an article of clothing were intended for use or would be effective in the treatment of open wounds such as sores, cold sores, cutaneous openings, ulcerations, lesions, abrasions and burns.

In WO 01/81671 there is described that textile fabrics incorporating fibers coated with a cationic form of copper are also effective for the inactivation of antibiotic resistant strains of bacteria and said cationic species of copper preferably comprises $Cu^{++}$ ions, however, also in this specification, the textile fabrics were described for use in treating a hospital environment to prevent the spread of infection by the inactivation of such bacteria excreted by an infected patient and said specification did not teach or suggest that an article of clothing formed from such a textile fabric would be effective for preventing, minimizing and removing wrinkles and providing for smoother and more robust skin surfaces.

In WO 01/74166 there is described and claimed the use of particles which release $Cu^{++}$ for the preparation of a polymeric material having microscopic particles which release $Cu^{++}$ encapsulated therein with a portion of said particles being exposed and protruding from surfaces thereof, said polymeric material being effective to inhibit HIV-1 proliferation, however, said publication was limited to the teaching of the use of such polymeric materials for the preparation of condoms and possibly gloves and the inventor thereof did not realize at said time and said publication does not teach or suggest the present inventive concept of providing an article of clothing which would be effective for preventing, minimizing and removing wrinkles and providing for smoother and more robust skin surfaces.

In U.S. Pat. No. 5,848,592, U.S. Pat. No. 5,492,882, French patent 2764518, British Patent 1382820 and U.S. Pat. No. 5,217,626 there are variously disclosed air or water filters comprising copper metal, copper oxides, chloride, carbonate and sulfate against noxious vapors and gases and against bacteria and viruses. In the case of British Patent 1382820 a gas filter is disclosed incorporating active carbon and/or an oxide or oxides of one or more metals of a high molecular weight in order to physically block and prevent the passage of bacteria. In the case of U.S. Pat. No. 5,215,626 a water filter is disclosed incorporating a mixture of a permanganate compound, a silver compound and a water-soluble copper compound such as copper chloride or copper sulfate.

None of said references however, teach or suggest the use of fibers incorporating water-insoluble copper compounds which release $Cu^+$ ions, $Cu^{++}$ ions or combinations thereof upon contact with a fluid, for the manufacture of a fabric to be brought in contact with a body surface for preventing, minimizing and removing wrinkles and providing for smoother and more robust skin surfaces.

DATABASE WPI Section Ch, Week 199031 Derwent Publications Ltd., London, GB; Class BO4, An 1990-234808 XP002247181 & JP 02 161954 and DATABASE WPI Section Ch, Week 198821 Derwent Publications Ltd., London, GB; Class A88, An 1988-145060 XP002247182 & JP 63 1088007 relate to hollow porous fibres and especially JP 631088007 discloses treating body fluids with cellulose bound copper ammonium however neither of said references teach or suggest the use of fibers incorporating water-insoluble copper compounds which release $Cu^+$ ions, $Cu^{++}$ ions or combinations thereof upon contact with a fluid, for the manufacture of a fabric to be brought in contact with a body surface for preventing, minimizing and removing wrinkles and providing for smoother and more robust skin surfaces.

As stated hereinbefore WO 01/74166 teaches and claims an antimicrobial and antiviral polymeric material, having microscopic particles which release $Cu^{++}$ encapsulated therein and protruding from surfaces thereof but does not teach or suggest the method of the present invention. Similarly WO 01/81671 teaches and claims a method for combating and preventing nosocomial infections, comprising providing to health care facilities textile fabrics incorporating fibers coated with a cationic form of copper, for use in patient contact and care, wherein said textile fabric is effective for the inactivation of antibiotic resistant strains of bacteria and also does not teach or suggest the use of fibers incorporating water-insoluble copper compounds which release $Cu^+$ ions, $Cu^{++}$ ions or combinations thereof upon contact with a fluid, for the manufacture of a fabric to be brought in contact with a body surface for preventing, minimizing and removing wrinkles and providing for smoother and more robust skin surfaces.

Thus, none of the above publications teach or suggest the subject matter of the present invention.

In the method of the present invention the cationic species of copper must be exposed to a liquid medium to allow for atomic dispersion into the medium whether said medium is perspiration which acts as a carrier for said atomic dispersion, or a liquid or surfactant which is added to the fibers or fabric to facilitate the transfer of the ions to the skin surface to be treated.

In order to form a cosmetic material of the present invention for preventing, minimizing and removing wrinkles and providing for smoother and more robust skin surfaces, one would preferably take fibers having ionic copper selected from the group consisting of $Cu^+$ and $Cu^{++}$ ions and include them in a substrate. In a woven substrate, the fibers would be blended with any other fiber and woven or knit into a substrate. In a non-woven configuration the fibers would be blended to form a thin layer. In both cases, a number of layers could preferably be placed one on top of the other to form a pad.

The ionic copper used in the method of the present invention is prepared in a manner similar to that described in the earlier specifications referenced above with slight modifications as described hereinafter and is obtained through a redox reaction either on a substrate or alone in the liquid. The method of production is an adaptation of technology as used in the electroless plating of plastics, particularly printed circuit boards made of plastic, with metals. See, for example, Encyclopedia of Polymer Science and Engineering (Jacqueline I. Kroschwitz, editor), Wiley and Sons, 1987, vol. IX, pp 580-598. As applied to fibers or fabrics or membranes, this process includes two steps. The first step is the activation of the substrate by precipitating a catalytic noble metal nucleation sites on the substrate surface. This is done by first soaking the substrate in a solution of a low-oxidation-state reductant cation, and then soaking the substrate in a solution of noble metals cations, preferably a solution of Pd++ cations, most preferable an acidic $PdCl_2$ solution. The low-oxidation-state cation reduces the noble metal cations to the noble metals themselves, while being oxidized to a higher oxidation state. Preferable, the reductant cation is one that is soluble in both the initial low oxidation state and the final high oxidation state, for example Sn++, which is oxidized to Sn++++, or Ti+++. Which is oxidized to Ti++++.

The second step is the reduction, in close proximity to the activated substrate, of a metal cation whose reduction is catalyzed by a noble metal. The reducing agents used to reduce the cations typically are molecular species, for example, formaldehyde in the case of Cu++. Because the reducing agents are oxidized, the metal cations are termed "oxidant cations" herein. The metallized substrate thus produced is characterized in that their metal plating is bonded directly to the substrate.

Based on the process described above, it is also possible for someone familiar with the art to identify the oxidant states by their colors. When the substrate is allowed to float in a copper solution for reduction as described above, different colors are obtained on each side of the substrate. The topside of the substrate is the shiny bright copper (red/yellow) color characteristic of elemental copper—Cu. The bottom side of the fabric is a black color, which is characteristic of CuO. Any substrate located under the top substrate also shows a black shade on its upper side.

In the process described herein, changes are made to the process to allow the plating of a cellulose fiber or substrate with a different cationic species of copper than elemental copper or copper oxide (CuO—black).

This form of electro-less plating process involves the reduction of a cationic form of copper from a copper solution such as copper sulfate or copper nitrate on to a prepared surface on fibers or a substrate. The fibers or substrate to be plated must first be soaked in a solution containing at least one reductant cationic species having at least two positive oxidation states, then at least one cationic species being in a lower of the at least two positive oxidation states. The fibers or substrate are then soaked in a solution containing at least one noble metal cationic species, thereby producing an activated surface.

The fibers are then exposed to at least one oxidant cationic species in a medium in contact with the activated surface. A reducing agent is then added and the copper reduces itself from the solution on to the surface of the fibers. Without the following changes, the fibers or substrate produced using this formula demonstrates an elemental copper coating on the fibers which are on the top of the fiber or substrate pack and black colored fibers below and throughout the fiber or substrate pack.

As stated hereinbefore, in order to obtain a material that is effective for preventing, minimizing and removing wrinkles and providing for smoother and more robust skin surfaces a cationic species of copper must be obtained. The effective compounds of copper must contain either a Cu (I) or Cu (II) species or both. To insure obtaining these species on cellulose, the Pd++ must be applied so that there is equal saturation of all fibers at the same time, e.g. by soaking and squeezing. If a large fiber pack is dropped into the Pd++ solution, the first fibers to hit the solution will absorb more of the Pd++ solution than other parts of the pack, which will upset the cationic copper deposition. In addition, the fibers must be washed between the first process involving the Sn++ and the second process, Pd++, in water. Residual Sn++ solution left between the fibers will cause a reduction of the Pd++ directly into the solution between the fibers and will allow only a random reduction of the Pd++ on the fibers which will again effect the deposition of the copper. While these two points may seem small, they have a direct effect on the plating.

In addition, a change is necessary in the application system of the copper solution to the process. A side effect of the reduction process on to the fibers is the creation of hydrogen. This hydrogen appears as bubbles on the surface of the fibers. The hydrogen forms as a result of the interaction in the copper solution with the Pd++ on the fiber surface. If the hydrogen is not removed, by methods known per se, such as squeezing, from the surface of the fibers immediately upon their formation, the fibers exposed to the air will be coated with an elemental copper. The fibers just below the surface of the elemental copper will be black copper oxide. If, however, the hydrogen is removed immediately with their formation of the bubbles, the desired cationic species is obtained throughout the fiber pack. The desired color will be a dark brown which is distinct from the copper metal color or the black copper oxide. A further indication of the cationic species is that the fibers will not conduct electricity.

This process yields both a Cu (I) and a Cu (II) species as part of copper oxide compounds. Analysis of residual copper oxide powder formed by this process has shown that formed on the surface are copper oxide compounds which are 70% Cu (I), and 30% Cu (II). These compounds have been proven to be a highly effective in the treatment of sores abrasions and burns. The activity of the copper takes advantage of the redox reaction of the cationic species with water and allows a switch between Cu (II) and Cu (I) when there is contact with water. Cu (I) is more effective than Cu (II) against HIV while Cu (II) is more stable than Cu (I).

In U.S. patent application Ser. No. 10/339,886 corresponding to PCT/IL03/00230, the relevant teachings of which are also incorporated herein by reference there is described and claimed a device for the inactivation of a virus comprising a filtering material, said device having ionic copper selected from the group consisting of $Cu^+$ and $Cu^{++}$ ions and combinations thereof incorporated therein.

In said specification there is described the plating of cellulose fibers using a copper solution which results in the formation of copper oxide on the surface of said fibers wherein the process used yields both a Cu (I) and a Cu (II) species as part of a copper oxide molecule. Said fibers were then incorporated into a filter which was found to be effective in the inactivation of HIV-1.

While the mechanism of the hydrophilic polymeric materials according to the present invention is not fully understood, in light of the results obtained, it is believed that when the polymeric material is brought into contact with a fluid aqueous medium, said medium leaches the cationic species of copper from within said polymer and as described in PCT/IL03/00230 the wrinkle effecting activity takes advantage of the redox reaction of the cationic species with water and allows a switch between Cu (II) and Cu (I) when there is contact with water. Cu (I) is more effective than Cu (II) while Cu (II) is more stable than Cu (I). The Cu (II) compound will oxidize much more slowly than the Cu (I) compound and will increase the shelf life of the product.

As stated hereinbefore, the discovery of the present invention that materials incorporating water-insoluble copper compounds which release $Cu^+$ ions, $Cu^{++}$ ions or combinations thereof upon contact with a fluid are surprisingly effective in preventing, minimizing and removing wrinkles and providing for smoother and more robust skin surfaces enables the production of an entire new line of products according to the present invention.

Keeping in mind that the product will encourage better skin appearance no matter where the fabric touches the body, the following is a description of some products and the protocols for their end use:

1. A sock knit from either treated polymer or cellulose yarns that can be worn day or night as any other sock, which will yield fresher looking feet.
2. A knit glove that can be worn while sleeping that will reduce wrinkles and improve skin softness of the hands.
3. A face mask or eye-covering mask that can be worn while sleeping that will improve the facial skin.
4. A pajama made from fabrics either knit or woven that can be worn at night and that will improve general body skin.
5. A woven or knit scarf made from either cellulose or polymer fibers that can be worn day or night that will improve neck skin appearance.
6. An adhesive bandage that can be placed on specific pock marks to improve the texture of the skin at the mark.
7. A knit or woven undergarment whether panty, underwear or bra that can be worn day or night and will improve the skin texture of the specific area of the body with which it comes in contact.
8. Bed linens and sleepwear: These can be in the form of a textile made from either a cotton/polyester or cotton based fabric where a percentage (can vary from 3% to 10%) of the yarn is treated cellulose or where the fibers of the yarn are a polymer in either filament or staple form. The article can be knit such as a cast lining or sock or can be woven such as a head cover or other article of clothing.
9. Sheath for neck: These will preferably be made from the new breathable polymers that allow for the wicking and dispersion of moisture through them which polymers have been produced with the water insoluble cationic copper oxide particles introduced into the extrusion process.

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments, will serve to illustrate the practice of this invention, it being understood that the particulars shown are by way of example and for purposes of illustrative discussion of preferred embodiments of the present invention only, and are presented in the cause of providing what is believed to be the most useful and readily understood description of formulation procedures, as well as of the principles and conceptual aspects of the invention.

IN THE DRAWINGS

Figure 3:
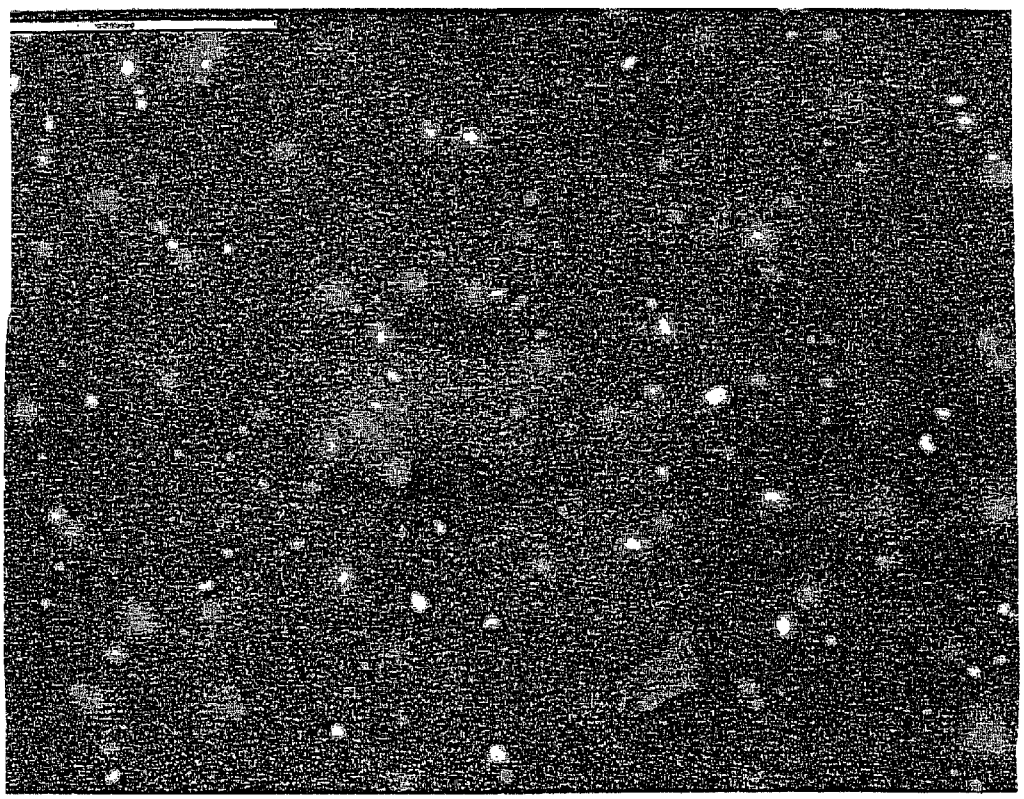
Figure 4:
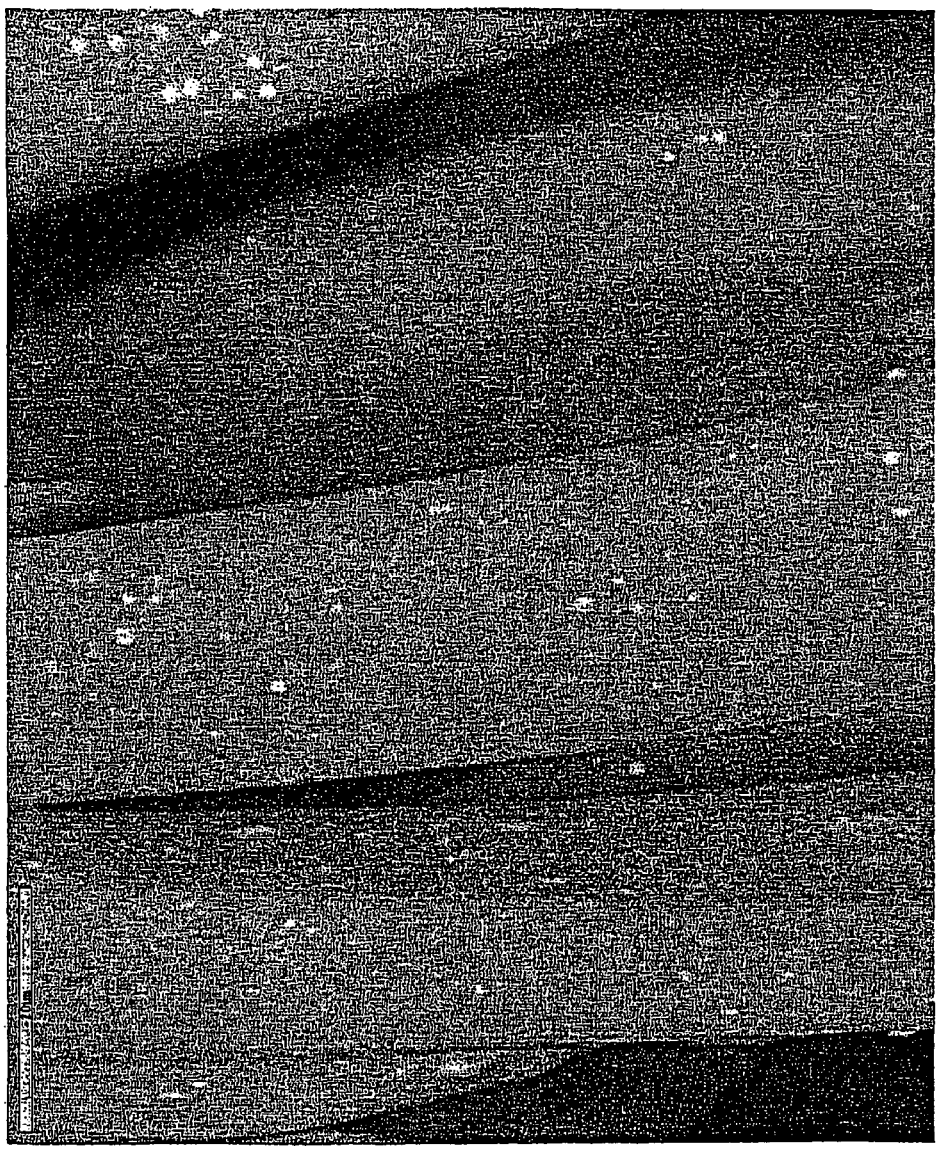
Figure 5:
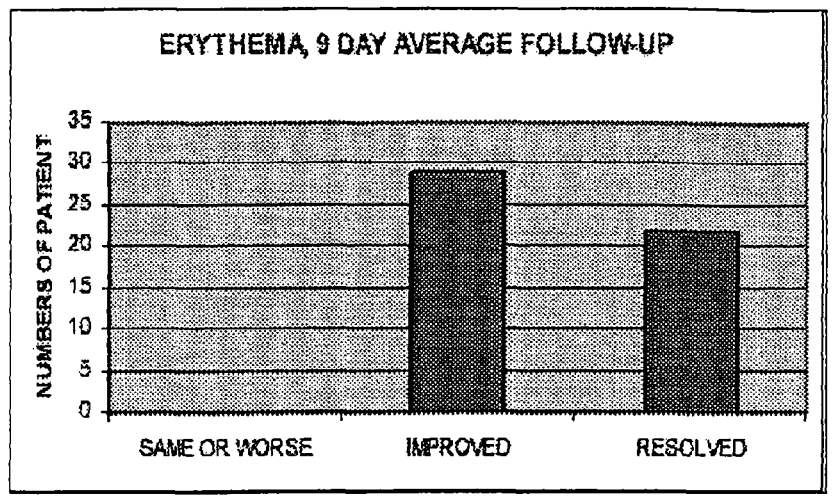
Figure 6:
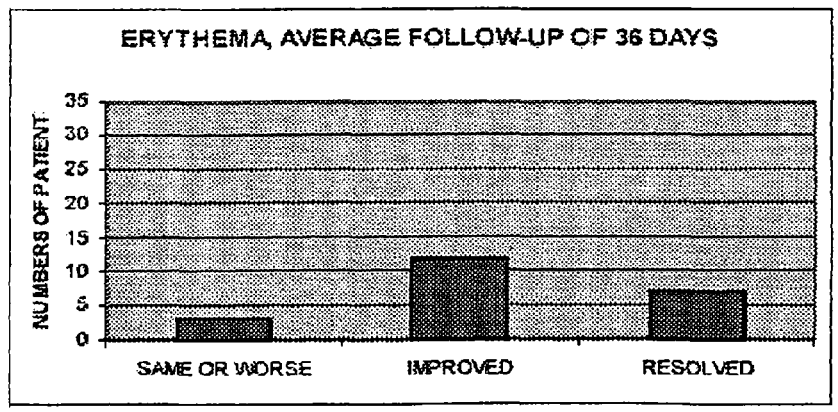
Figure 7:
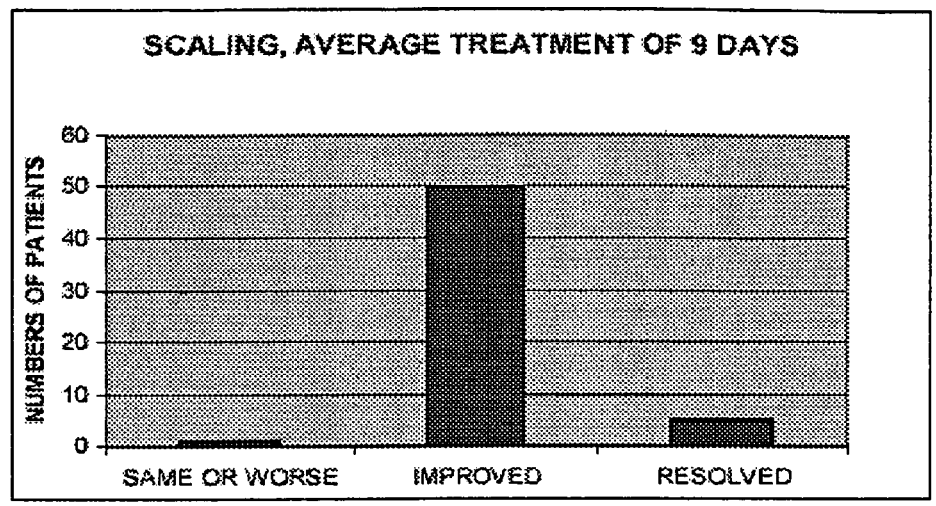
Figure 8:
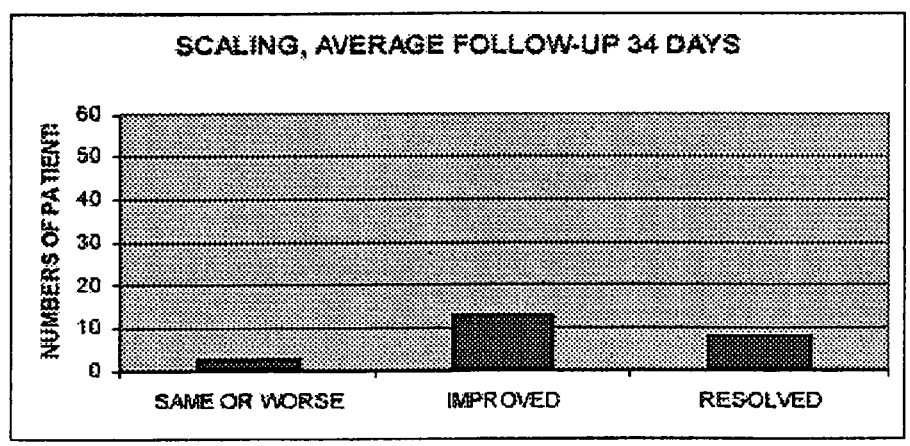
Figure 9:
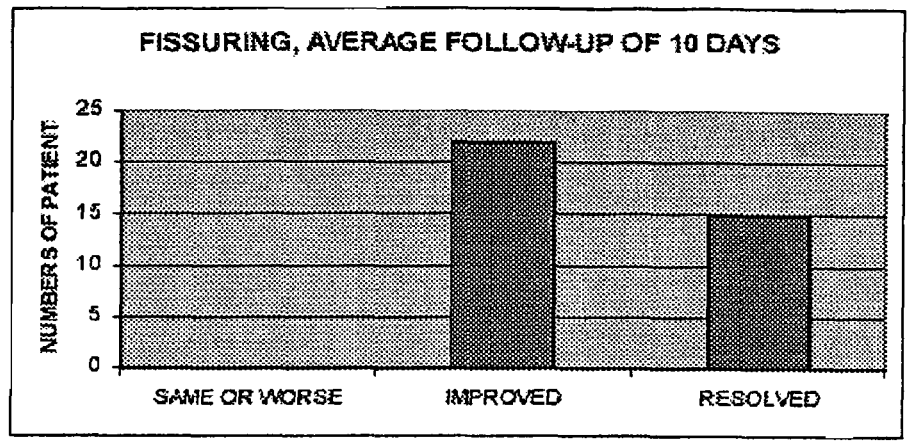
Figure 10:
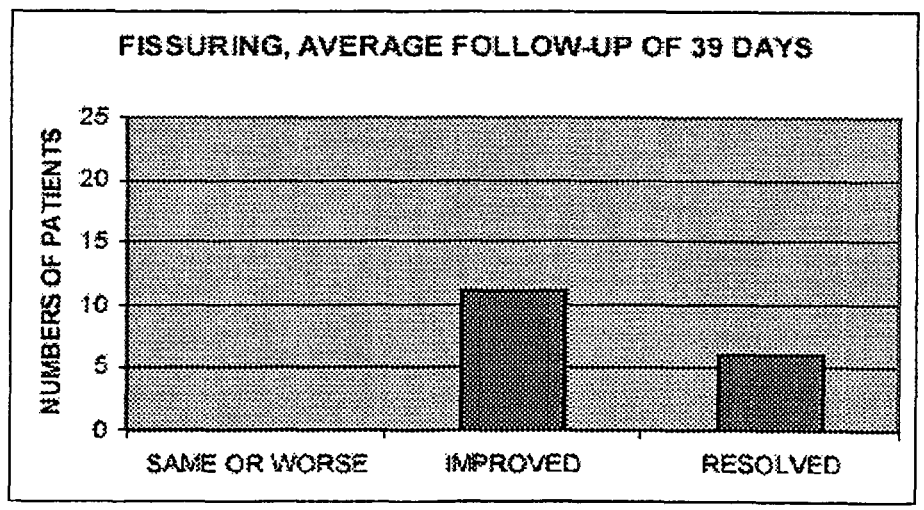

FIG. 3 is an electron microscope photograph of a polypropylene breathable film which was prepared by introducing 1% water insoluble copper oxide into the master batch before extrusion of the film, to form a film having microscopic water insoluble particles of ionic copper oxides in powdered form, embedded directly therein with a portion of said particles being exposed and protruding from surfaces thereof; and showing up as white dots in the electron microscope photograph thereof;

FIG. 4 is an electron microscope photograph of a polyester fiber prepared by introducing 1% water insoluble copper oxide into the master batch before extrusion of the fiber, to form fibers having microscopic water insoluble particles of ionic copper oxides in powdered form, embedded directly therein with a portion of said particles being exposed and protruding from surfaces thereof, and showing up as white dots in the electron microscope photograph thereof;

FIG. 5 is a graphical representation of a 9 day follow-up regarding Erythema;

FIG. 6 is a graphical representation of a 36 day follow-up regarding Erythema;

FIG. 7 is a graphical representation of a 9 day treatment regarding scaling;

FIG. 8 is a graphical representation of a 36 day follow-up regarding scaling;

FIG. 9 is a graphical representation of a 9 day follow-up regarding fissuring;

FIG. 10 is a graphical representation of a 39 day follow-up regarding fissuring, and;

FIG. 11 is a table setting forth the observed results on wrinkles of women using a pillowcase prepared according to the present invention.

EXAMPLE 1: PREPARATION OF FABRICS FROM TREATED CELLULOSE FIBERS

1st. A cellulose fiber is chosen for the desired end use. Such fibers as, Tencel, or acetate, or viscose or raw cotton are among the fibers that can be used. It is necessary to note that the fibers must be cellulose based as the plating will use the OH groups on the surface for initial attachment to the fiber. The length of the fiber chosen is a function of the end use and is common knowledge in the industry (i.e. long staple fibers are mixed with other fibers that have the same length such as in the case of combed cotton, etc.).

2nd. The fibers pass through the various chemical processes as described herein:

1. Fibers are prepared in a thin mat to assure a deposition of the correct cationic species.
2. The mat is soaked in a solution of Tin Dichloride and hydrochloric acid. The mat is allowed to soak for a small amount of time to insure complete absorption.
3. The mat is then squeezed to remove almost all liquid and washed in water to assure the removal of all the tin solution.
4. The mat is then placed in a very dilute solution of palladium dichloride and hydrochloric acid. While other metal salts can be used for this process, palladium was found to be the most efficient.
5. After removal from the palladium dichloride the mat is once again washed and again squeezed to assure the removal of all extraneous liquid. At this point the mat will have changed color to a light tan.
6. A chelated copper sulfate solution is prepared using copper sulfate, polyethylglycol, and EDTA. The pH of the solution is controlled by adding sodium hydroxide to the solution. A reductant is added to the copper sulfate solution. While many reductants can be used formaldehyde was chosen as the preferred compound.
7. The mat is placed in the solution and allowed to go through the process which can take up to 7 minutes to occur. The mat must be squeezed or patted down during the plating process.
8. The mat is then washed in water to remove excess dust and allowed to dry.
9. At the end of the process, the fibers are plated with an ionic form of copper and have a dark brown mixed shade color.
10. The fibers are blended with other fibers (the same untreated or other fibers) so that the end product contains only the amount of the desired copper oxide plated fibers. In some cases a 1% blend/99% other fibers is necessary and in other cases as much as 30% treated fibers/70% other fibers or any combination is prepared. This can be done in several ways all known to people familiar with the art of textile yarn spinning.
11. The mixed fibers run through all normal textile processes, i.e. in the case of an open-end spun product: carding, sliver, spinning.
12. Once yarn is obtained it can be either woven or knit depending on the desired end-use.
13. Fabrics can be used as are or they can then be dyed or printed but not bleached, as this will cause the copper to disconnect itself from the cellulose substrate.
14. The textile fabric can than be easily converted into the desired product.

EXAMPLE 2: PREPARATION OF FABRICS OR FILMS FROM TREATED POLYMERIC MATERIALS

Example 2a: Preparation of Fabrics

A1. A polymeric material is chosen for the desired end use. Such fibers as polyester, polypropylene, polyethylene, nylon 66, nylon 6, etc. are among the fibers that can be used. The fiber can be formed into either a filament form or short staple form.

A2. A master batch is prepared using the same base material as the desired yarn into which a copper oxide powder is added. For most textile end uses the master batch may have a 20%-25% concentration of the copper oxide powder included in it. This master batch will be added to the polymer being extruded and diluted so that only about 1% or 2% of the material will be in the finished yarn. A certain amount of this copper will appear on the surface of a polymeric fiber and can be observed in an electron microscope picture.

A3. If the fiber is a filament fiber it can be woven or knit to produce a textile.

A4. If the fiber is a staple fiber it can be mixed with other fibers just the way the coated fibers described above are mixed and then follow the same process of manufacturing.

A5. Once yarn has been completed, it can woven or knit into a textile product which follows the normal and accepted systems for finished product conversion.

Example 2b: Preparation of Films or Sheaths

B1. A polymeric material is chosen for the desired end use. Such polymers as polyester, polypropylene, polyethylene, nylon 66, nylon 6, etc. are among the polymers that can be used. The polymeric material can be formed into either a film, or a sheath.

B2. A master batch is prepared using the same base material as the desired polymer into which a copper oxide powder is added. For most end uses the master batch may have a 1-3% concentration of the copper oxide powder included in it. This master batch will be added to the polymer being extruded. A certain amount of this copper will appear on the surface of a polymeric film or sheath and can be observed in an electron microscope picture.

Example 2C: Preparation of Fibers

A total of 500 grams of a polyamide bi-component compound were prepared by heating the two beaded chemicals in separate baths each at 160° C.

The two separate components were then mixed together and allowed to stir for 15 minutes until the mixture appeared to be homogenous in color.

The mixed chemistry was again divided into two separate pots. In one pot, 25 grams of a mixture of CuO and $Cu_2O$ powder was added yielding a 1% mixture. In the second pot 6.25 grams of a mixture of CuO and $Cu_2O$ were added yielding a 0.25% mixture. In both cases, the temperature of 160° C. was maintained. The compounds were stirred until they appeared homogenous in color.

The two mixtures were run through a spinneret with holes that yielded fibers of between 50 and 70 microns in diameter. Since the Cu++ releasing copper oxide powders were ground to particles of less than 20 microns no obstructions in the spinneret holes were observed. The extruded fibers were air-cooled and spun on to cones.

The resulting nylon fibers having Cu++ releasing copper oxide incorporated therein can be used in many of the applications of the present invention including in gloves or socks, and scarves.

As will now be understood by persons skilled in the art, the difference between the normal process of manufacturing any synthetic fiber and this process, is the addition of the Cu++ releasing copper oxide powders in the raw materials, and for many uses of the present invention such polymers as polyester, nylon and polypropylene can be interchangeably used.

EXAMPLE 3: REGENERATION OF HEEL AREA OF FOOT

Figure 1A:
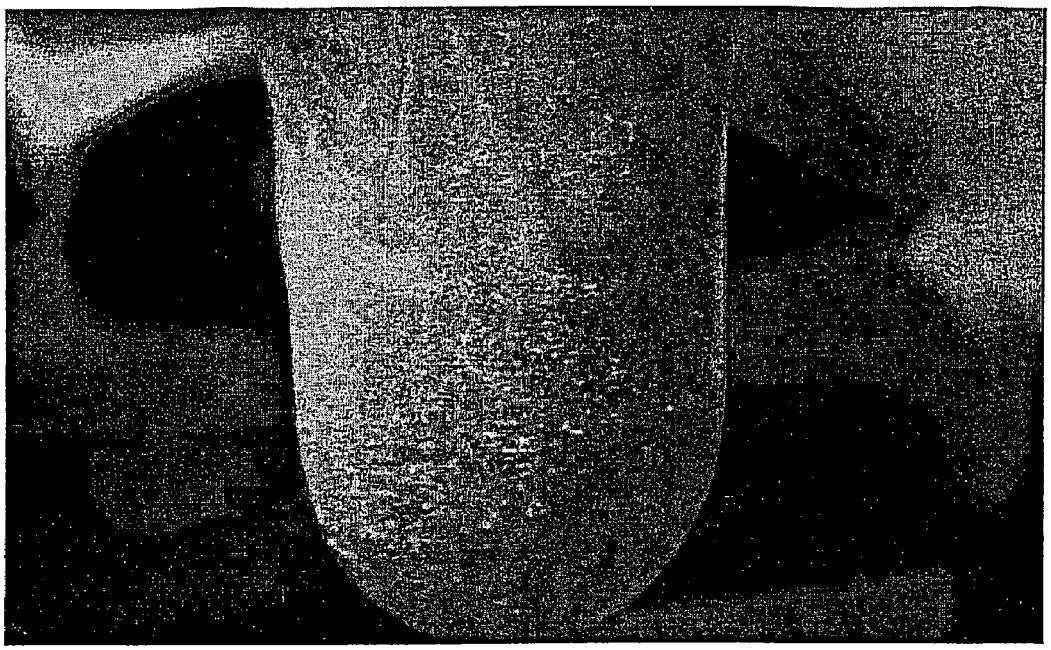
FIG. 1a and FIG. 1b are photographs of the heel of a foot of a patient taken before and after application thereto of a sock according to the present invention as described in example 3 hereinafter.
Figure 1B:
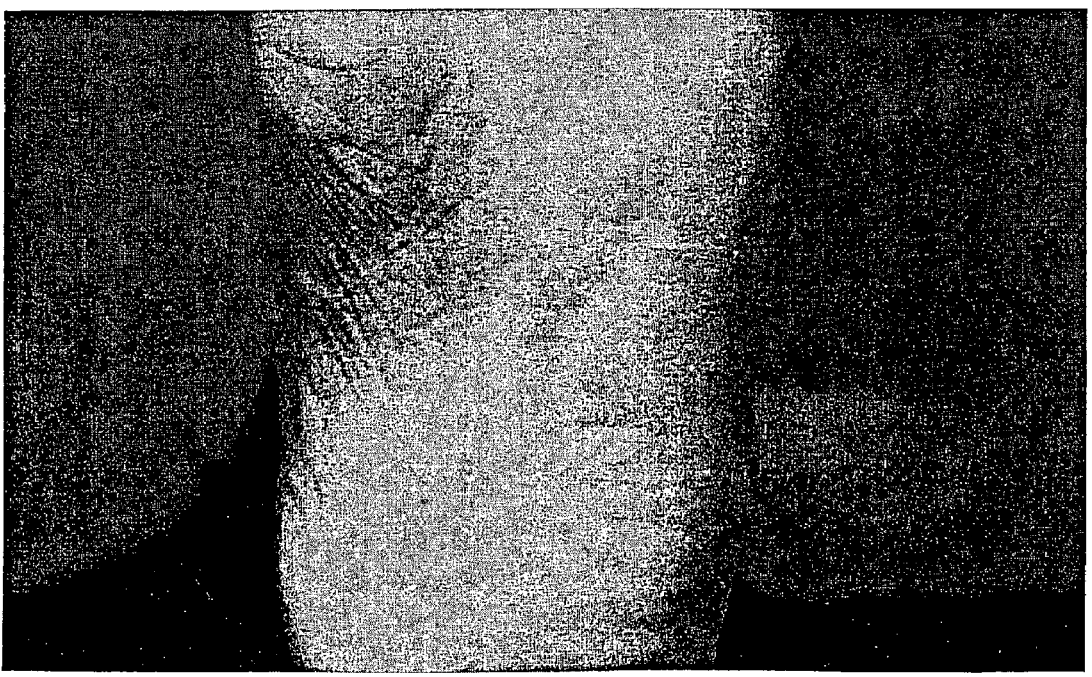

Referring to FIGS. 1a and 1b, there are seen before and after photographs of the heel and sole area of a foot of a volunteer, wherein in FIG. 1a it can be seen that said area is wrinkled and patchy. A polyester sock according to the present invention having 1% of fibers of insoluble copper oxide compounds of $Cu^+$ and $Cu^{++}$ incorporated into the bottom toe and heel area thereof was worn for 6 days. At the end of said period a further photograph was taken as seen in FIG. 1b, and as can be seen the skin is more robust, softer, less patchy and has fewer wrinkles even though this is not readily seen in the attached black and white photograph.

EXAMPLE 4: REDUCTION IN WRINKLES IN BACK OF HAND SURFACES

Figure 2A:
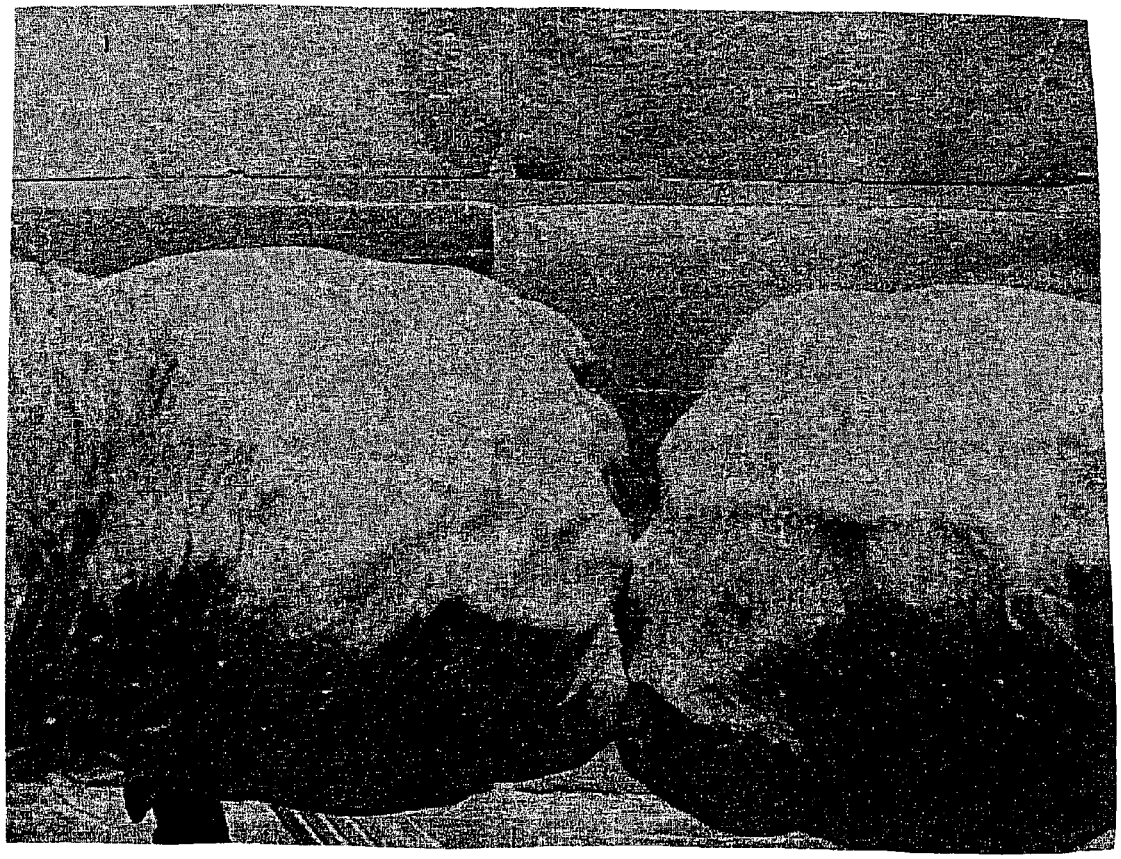
FIG. 2a and FIG. 2b are photographs of the two hands of a volunteer taken before and after wearing a pair of gloves according to the present invention as described in example 3 hereinafter.
Figure 2B:

Referring to FIG. 2a, there is seen a photograph of both hands of a volunteer. Said volunteer then wore a cotton glove according to the present invention on his left hand only, for a period of 3 nights and for about 10 hours each night. Said glove was made of 97% cotton and included 3% of cellulose fibers according to the present invention, wherein said fibers were coated with insoluble copper oxide compounds of $Cu^+$ and $Cu^{++}$. As can be seen in FIG. 2b, after only 3 days the left hand of the user was much smoother and the wrinkles were much less pronounced.

EXAMPLE 5: CLINICAL TESTING

Dr. Michael S. Smith, a Board Certified Neurologist with a Master's Degree in Experimental Statistics, was asked to analyze the effectiveness of socks prepared with a lower panel of fabric incorporating water-insoluble copper compounds which release $Cu^+$ and $Cu^{++}$ ions, upon a variety of podiatric conditions, i.e. erythema, scaling, fissuring, odor and edema. Other indications such as itching and burning, vesicular eruptions and drainage were noted and recorded although these are not cosmetic issues.

One group of patients was studied; and the results were compared to the experience the podiatrist had with patients with similar conditions who were not treated with socks according to the present invention.

Results:

The following results are all considered statistically significant, meaning that there is credible medical evidence that treatment with the socks according to the present invention is effective in the period of follow up studied, since the confidence interval of all the results did not include 0 and the p-values for all results were <0.001.

Demographics:

There were 56 patients in all, 17 women and 39 men. The average age of the group was 58 with a standard deviation of 16 years (range 21-85 years). Twenty-one (21) were diabetic, 21 were older than 65, and 24 were followed more than one time.

Variables:

Seven measures were studied: erythema, burning and itching, edema, scaling, vesicular eruptions, fissuring, drainage and odor. Only scaling was present in all 56 patients, with erythema in 51 (see table). Edema (6), Odor (5), and drainage (3) were the least common variables. "Long range follow-up referred to having been evaluated more than one time after use of the socks. There was a three level ordinal scale used: present, improvement, and resolved. Movement along this scale (from "present" to "improved" or from either of the first two to "resolved") was considered a positive sign, movement the other way (from "improved" to "present") considered a negative sign. If a patient was considered resolved on the first visit after wearing the socks, that individual could at best be scored a "same" for long-term follow-up. Therefore, "same" could be equally considered to be "holding improvement". The average length of time in the long term section was defined as being the time between the first visit and the date when the last comment was made about the patient. Only patients who had a specific problem at the outset of the study were counted later. In no instance, did a patient who had no specific problem develop one. In the instances of edema, odor, and drainage, the sample sizes were too small to draw any conclusions, although the results were tabulated.

Example 5A: Erythema (51 Patients)

A1. All 51 patients improved; 22 (42%) resolved completely over an average period of 9 days (range 4-28 days). The 95% confidence interval for resolution was (0.29, 0.58). This result means that while we don't know the percent of complete resolution for the entire population (the parameter), we are highly confident it lies in the interval between 29% and 58%. If we know in advance that no patient would normally improve without other treatments in this time frame, than the results obtained are highly significant; that is, not due to chance.

The results of this test are shown in FIG. 5.

A2. Longer term study (22 patients):

Nineteen (86%) maintained their improvement or resolved, 95% Cl (0.65, 0.97). Three patients (14%) did not maintain improvement or reverted to "present", 95% Cl (0.03, 0.34). The average length of follow-up was 36 days. Diabetics and patients older than 65 shared in the improvement, both early and long-term.

The results are shown in FIG. 6.

Example 5B: Scaling (56 Patients)

B1. Fifty-five (55) of the 56 improved (98%), 5 resolved (9%), and 1 stayed the same. The 95% confidence interval for some improvement is (0.90, 1.00); for resolution (0.03, 0.20). Both of the p-values are highly significant for efficacy.

The results are shown in FIG. 7.

B2. Longer term study (24 patients):

Twenty-one (88%) held improvement or resolved, 3 reverted with an average follow-up of 34 days. The 95% confidence interval is (0.68, 0.97) with a p-value <0.001. Again, diabetics and elderly shared in the improvement.

The results are shown in FIG. 8.

Note: the follow-up graph has the same scale as the former graph to facilitate comparison.

Example 5C: Fissuring (37 Patients)

C1. All 37 patients improved; 15 (40%) resolved completely with an average follow-up of 10 days, 95% Cl (0.25, 0.58). This is highly significant.

The results are seen in FIG. 9.

C2. Longer term study (17 patients):

All 17 patients improved, 6 (35%) resolved completely in an average follow-up of 39 days, 95% Cl (0.14, 0.62). Again, diabetics and elderly shared in the improvement. The results are seen in FIG. 10.

Example 5D: Edema (6), Drainage (3), and Odor (5)

Three patients with edema improved; 1 resolved. All three patients with drainage improved; 2 resolved. Three of the five patients with odor improved; two of them resolved.

Discussion:

The purpose of the study was to see if patients with a variety of podiatric ailments would improve only by wearing socks having a fabric panel according to the present invention. One issue in the treatment of the above conditions is compliance in obtaining and using the treatment (special socks). A related issue is the proper application of treatment (special socks) on the plantar aspect of the feet and in the interdigital areas.

1. For purposes of these examples the following was assumed in the analysis of the data provided:
   a. The patients were a reasonable, representative sample of the population of patients with these conditions. There was no information received that would contradict this assumption. There were men, women, elderly, young, diabetic, and non-diabetic patients.
   b. The patients were independent of one another; that is, the selection of one individual had no effect upon the selection of another.
   c. The definitions of improvement and resolution were constant for each patient.
   d. The sample size was known and appropriate to perform analysis.
   e. Outcomes could be defined as dichotomous.
   The presence of these assumptions allowed a binomial probability distribution to be used.
2. There was no control group reported; however, information was received stating that the podiatrist believed it unlikely that any patient would have resolved or improved in the time frame of the study only by wearing his or her regular socks. Given such information, all of the above results, would be considered statistically significant, meaning that there is medical evidence that treatment with fabric panels according to the present invention is effective in this period of follow-up.

It is important to understand the vocabulary used in describing the study:

Population: the group about which one wishes to learn. In this instance, the population are all patients with the above listed foot conditions.

Sample: a subset of a population.

Random sample: A subset chosen where each member of the population has a defined, non-zero probability of being chosen.
Parameter: a numerical measure of the population.
Statistic: a numerical measure of the sample.
p-value: the probability that we would obtain the specific sample statistic (or one more extreme) if the null hypothesis (hypothesis of no change) were true. In the context of this study, a p-value of less than 0.001 means that the probability of obtaining these results by chance alone is less than 1 in 1000. Typically, 1 in 20 is considered the "cut-off" point. Minitab software does not compute p-values to four decimal places, so many of the values obtained here are even smaller.
A confidence interval contains a range of plausible values for the parameter. We call it a confidence interval, because while unknown, the parameter does exist, and the interval either contains or does not contain the parameter. It is NOT a probability question. For this study, if we assume that no patient would improve in the time frame studied with conventional treatment then so long as the interval does not contain 0, the results are significant, since no plausible value of the parameter is 0. If some other proportion were postulated for improvement, then any interval that did not contain that particular value would be considered significant. In this study, with the above information, all areas reached statistical significance.
Circle of inference: We sample from a population, obtain a result (a statistic), and use that value to infer something about a parameter which is part of a population.

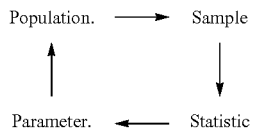

It is important to recognize that one can seldom identify all members of a population, so that its numerical measure, a parameter, remains unknown.

For this study, since we cannot know all members of the population, the result of the sample, the proportion improved (or resolved), is used to say a similar proportion of the population would be improved as well. If the sample is appropriately chosen, then the estimate has value. We must realize, of course, that other samples would lead to other results, so that there is a range of plausible values that samples could conceivably have, and our sample result was one of those potential values, as described above.

Conclusion:

Compared to historical controls, patients with socks prepared with a lower panel of fabric incorporating water-insoluble copper compounds which release $Cu^+$ and $Cu^{++}$ ions as according to the present invention, had significant improvement or resolution in the following conditions:
Erythema
Fissures
Scaling
Edema
Odor Moreover, since nearly 40% (19 of 51) of the group was either diabetic or older than 65 (10 were both diabetic and older than 65), this study is statistically significant for improvement or resolved for all the above conditions for people with diabetes, including elderly diabetics.

As is known, erythema is characterized by a redness of the skin caused by dilatation and congestion of the capillaries and is often a sign of inflammation or infection, and therefore is a cosmetic concern;

Scaling is a healing issue when it relates to psoriasis of a microbial nature which is ameliorated by the use of the products of the present invention and is certainly a cosmetic issue.

Edema is an observable swelling in certain parts in the body and most commonly occurs in the feet and legs where it also is referred to as peripheral edema. The swelling is the result of the accumulation of excess fluid under the skin in the spaces within the tissues that are outside of the blood vessels and the reduction thereof is facilitated by the method and products of the present invention.

Fissuring is a break in the skin usually where it joins a mucous membrane producing a crack-like sore or ulcer and this is also a cosmetic issue which can be dealt with according to the present invention.

Odor is a major cosmetic issue which can be dealt with, with the products and methods of the present invention.

EXAMPLE 6: A STUDY OF THE EFFECT OF A PILLOWCASE ON FACE WRINKLES

Seventeen (17) women who regularly use skin treatment products were given a pillowcase which was formed from a fabric having fibres incorporating water-insoluble copper compounds which release $Cu^+$ ions, $Cu^{++}$ ions or combinations thereof upon contact with a fluid and were asked to be photographed before the test, at the end of the 1st week, at the end of the 2nd week, and again at the end of 4th week after sleeping each night with a pillow case prepared according to the present invention. At the end of the $8^{th}$ week the candidates were asked to telephone and notify the receiver of the information if there was an improvement or deterioration in overall skin appearance. The candidates were asked not to use any nightly oils or creams but just to wash off the face before going to sleep at night. The purpose of the evaluation was to observe the effect of the pillowcase on crow's feet, fine wrinkles and fine lines on the face only. The method of observation was photographic using a 3.4 psi digital camera in natural light.

Candidates were instructed to keep the pillowcase in contact with either side of the face when sleeping. The pillowcases were washed once a week in all cases. The candidates were instructed to wash their face with the same soaps that they normally use but not to use any oils or fresheners before going to sleep.

All candidates were aged between 45 and 60. None of the candidates were on medication. At least 2 of the candidates are known to be smokers.

For the purpose of the test, a dermatologist was asked to observe if there were any possible negative effects. No negative effects were observed which confirms the biocompatibility tests done previously. A panel of 10 different women were asked to evaluate the photographs with the following values:
1. No improvement symbolized by "A" on the attached sheet
2. Slight improvement symbolized by "B" on the attached sheet
3. Improvement symbolized by "C" on the attached sheet
4. Marked improvement symbolized by "D" on the attached sheet The names of the 17 candidates are available in a separate file and on the chart attached hereto as FIG. 11 are represented as numbers 1-17. The names of the 10 judges are available on a separate file.

As can be seen from the results recorded by these independent judges, as shown in FIG. 11, over time analysis of the face showed overall significant improvement for the reduction of crow's feet wrinkles, fine lines, and in some cases mottled hyper-pigmentation (liver spots). In all cases there was an overall improvement in skin appearance and texture.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A cosmetic method comprising applying a polymeric material daily during a treatment period to a face and/or neck of a subject identified as in need of reduction in wrinkles, fine lines, and/or crow's feet on the face or neck, wherein the polymeric material has particles of water-insoluble copper compounds embedded therein, wherein a portion of the particles of water-insoluble copper compounds are exposed and protruding from surfaces of the polymeric material, wherein the particles of water-insoluble copper compounds release Cu+ ions, Cu++ ions or combinations thereof upon contact with a fluid.

2. The method according to claim 1, wherein the polymeric material is a fabric.

3. The method according to claim 1, wherein the polymeric material is a polymeric film and the particles of water-insoluble copper compounds are in powdered form.

4. The method according to claim 1, wherein the polymeric material is a polymeric fiber.

5. The method according to claim 1, wherein the polymeric material is a polymeric filament.

6. The method according to claim 1, wherein the polymeric material is a polymeric sheath.

7. A cosmetic method according to claim 1, wherein the polymeric material is incorporated in a pillowcase.

8. A cosmetic method according to claim 1, wherein the polymeric material is incorporated in one of a bed sheet, an at least partial face mask, a scarf, a tubular sheath for removable positioning on the neck of a user the subject such that the neck of the subject is encircled by the tubular sheath, or an elongated panel having interlocking means provided at opposite ends thereof for adjustable attachment surrounding that is adjustably attachable to a body portion of a user the subject.

9. A cosmetic method according to claim 1, wherein the polymeric material is formed from a polymeric component comprising at least one of a polyamide, a polyester, an acrylic and a polyalkylene, the polymeric material being in the form of a fiber, a yarn, a sheath, a filament, or a sheet.

10. The method according to claim 1, wherein the polymeric material is a polymeric film and the polymeric film has the ability to disperse liquid through osmosis.

11. The method according to claim 1, wherein the polymeric material is a polymeric film and the polymeric film has micro pores perforated throughout to allow for the escape of excess liquids.

12. The method according to claim 1, wherein the polymeric material is a hydrophilic polymeric material.

13. The method according to claim 1, wherein the polymeric material is a hydrophobic polymeric material.

14. The method according to claim 1, further comprising evaluating the subject's face and/or neck after the treatment period, wherein the treatment period is at least two weeks applying the polymeric material for reduced wrinkles, fine lines and/or crow's feet as compared to prior to an initial application of the polymeric material.

15. The method according to claim 14, further comprising detecting a reduction in wrinkles.

16. The method according to claim 1, further comprising evaluating the subject's face and/or neck after the treatment period, wherein the treatment period is at least four weeks applying the material for reduced wrinkles, fine lines and/or crow's feet as compared to prior to an initial application of the material.

17. The method according to claim 16, further comprising detecting a reduction in wrinkles.

* * * * *